(12) United States Patent
Melik et al.

(10) Patent No.: US 8,323,257 B2
(45) Date of Patent: Dec. 4, 2012

(54) ABSORBENT ARTICLES COMPRISING A SLOW RECOVERY STRETCH LAMINATE AND METHOD FOR MAKING THE SAME

(75) Inventors: David Harry Melik, Cincinnati, OH (US); Janet Neton, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 779 days.

(21) Appl. No.: 12/274,795

(22) Filed: Nov. 20, 2008

(65) Prior Publication Data

US 2009/0134049 A1 May 28, 2009

Related U.S. Application Data

(60) Provisional application No. 61/003,954, filed on Nov. 21, 2007.

(51) Int. Cl.
*A61F 13/15* (2006.01)
*A61F 13/20* (2006.01)

(52) U.S. Cl. .......... 604/385.27; 604/385.21; 604/385.01

(58) Field of Classification Search ............. 604/385.01, 604/385.27, 367
See application file for complete search history.

(56) References Cited

U.S. PATENT DOCUMENTS

| | | |
|---|---|---|
| 3,086,242 A | 4/1963 | Cook et al. |
| 3,139,468 A | 6/1964 | Wheat |
| 3,370,630 A | 2/1968 | Gordon et al. |
| 3,587,581 A | 6/1971 | Jones, Sr. |
| 3,592,946 A | 7/1971 | Griffith |
| 3,601,923 A | 8/1971 | Rosenberg |
| 3,639,917 A | 2/1972 | Althouse |
| 3,819,401 A | 6/1974 | Massengale et al. |
| 3,848,594 A | 11/1974 | Buell |
| 3,860,003 A | 1/1975 | Buell |
| 3,911,173 A | 10/1975 | Sprague, Jr. |
| 3,912,565 A | 10/1975 | Koch et al. |
| 3,929,135 A | 12/1975 | Thompson |
| RE28,688 E | 1/1976 | Cook |

(Continued)

FOREIGN PATENT DOCUMENTS

CH 528285 2/1968

(Continued)

OTHER PUBLICATIONS

*Polymer Handbook*, Third Edition; Wiley Interscience; Section VII pp. 519-559.

(Continued)

*Primary Examiner* — Michele M Kidwell
(74) *Attorney, Agent, or Firm* — Richard L. Alexander; John G. Powell

(57) ABSTRACT

An absorbent article may comprise a topsheet, a backsheet joined with the topsheet, an absorbent core interposed between the topsheet and backsheet; and a slow recovery stretch laminate. The slow recovery stretch laminate may be joined to one or more article elements selected from the group consisting of the topsheet, the backsheet, the core, an anal cuff, an elasticized topsheet, a fastening system, a leg cuff, a waist elastic feature, a side panel, an ear, and combinations thereof. The slow recovery stretch laminate may exhibit an unload force at 37° C. of about 0.16 N/(g/m) or greater and a percent of initial strain after 15 seconds of recovery at 22° C. of about 10% or greater. And, the slow recovery stretch laminate may comprise an elastic member that was pretreated prior to and/or during draw down of the elastic member.

20 Claims, 5 Drawing Sheets

U.S. PATENT DOCUMENTS

| | | | |
|---|---|---|---|
| 4,054,616 A | 10/1977 | Miki et al. |
| 4,089,913 A | 5/1978 | Miki et al. |
| 4,116,842 A | 9/1978 | Meier |
| 4,122,134 A | 10/1978 | Miki et al. |
| 4,152,370 A | 5/1979 | Moczygemba |
| 4,169,336 A | 10/1979 | Kuhn |
| 4,248,981 A | 2/1981 | Milkovich et al. |
| 4,248,982 A | 2/1981 | Bi et al. |
| 4,248,984 A | 2/1981 | Bi et al. |
| 4,259,220 A | 3/1981 | Bunnelle et al. |
| 4,324,246 A | 4/1982 | Mullane et al. |
| 4,337,771 A | 7/1982 | Pieniak et al. |
| 4,342,314 A | 8/1982 | Radel et al. |
| 4,346,198 A | 8/1982 | Doak et al. |
| 4,381,781 A | 5/1983 | Sciaraffa et al. |
| 4,412,087 A | 10/1983 | Trepka |
| 4,418,180 A | 11/1983 | Heinz et al. |
| 4,450,026 A | 5/1984 | Pieniak et al. |
| 4,463,045 A | 7/1984 | Ahr et al. |
| 4,515,595 A | 5/1985 | Kievit et al. |
| 4,573,986 A | 3/1986 | Minetola et al. |
| 4,603,155 A | 7/1986 | Muramori et al. |
| 4,609,191 A | 9/1986 | Remme |
| 4,609,518 A | 9/1986 | Curro et al. |
| 4,610,678 A | 9/1986 | Weisman et al. |
| 4,629,643 A | 12/1986 | Curro et al. |
| 4,636,207 A | 1/1987 | Buell |
| 4,662,875 A | 5/1987 | Hirotsu et al. |
| 4,673,402 A | 6/1987 | Weisman et al. |
| 4,681,580 A | 7/1987 | Reising et al. |
| 4,695,278 A | 9/1987 | Lawson |
| 4,698,242 A | 10/1987 | Salerno |
| 4,699,622 A | 10/1987 | Toussant et al. |
| 4,699,941 A | 10/1987 | Salerno |
| 4,704,115 A | 11/1987 | Buell |
| 4,704,116 A | 11/1987 | Enloe |
| 4,704,434 A | 11/1987 | Kitchen et al. |
| 4,710,189 A | 12/1987 | Lash |
| 4,719,261 A | 1/1988 | Bunnelle et al. |
| 4,720,415 A | 1/1988 | Vander Wielen et al. |
| 4,761,198 A | 8/1988 | Salerno |
| 4,785,996 A | 11/1988 | Ziecker et al. |
| 4,787,897 A | 11/1988 | Torimae et al. |
| 4,795,454 A | 1/1989 | Dragoo |
| 4,808,178 A | 2/1989 | Aziz et al. |
| 4,816,025 A | 3/1989 | Foreman |
| 4,816,094 A | 3/1989 | Pomplun et al. |
| 4,820,590 A | 4/1989 | Hodgson, Jr. et al. |
| 4,834,735 A | 5/1989 | Alemany et al. |
| 4,842,666 A | 6/1989 | Werenicz |
| 4,846,815 A | 7/1989 | Scripps |
| 4,857,067 A | 8/1989 | Wood et al. |
| 4,874,255 A | 10/1989 | Ball et al. |
| 4,888,231 A | 12/1989 | Angstadt |
| 4,892,536 A | 1/1990 | Desmarais et al. |
| 4,894,060 A | 1/1990 | Nestegard |
| 4,900,317 A | 2/1990 | Buell |
| 4,909,803 A | 3/1990 | Aziz et al. |
| 4,938,753 A | 7/1990 | Van Gompel et al. |
| 4,939,208 A | 7/1990 | Lanza et al. |
| 4,940,464 A | 7/1990 | Van Gompel et al. |
| 4,946,527 A | 8/1990 | Battrell |
| 4,963,140 A | 10/1990 | Robertson et al. |
| 4,965,122 A | 10/1990 | Morman |
| 4,968,312 A | 11/1990 | Khan |
| 4,981,747 A | 1/1991 | Morman |
| 4,987,194 A | 1/1991 | Maeda et al. |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,026,364 A | 6/1991 | Robertson |
| 5,028,646 A | 7/1991 | Miller et al. |
| 5,036,978 A | 8/1991 | Frank et al. |
| 5,037,416 A | 8/1991 | Allen et al. |
| 5,047,484 A | 9/1991 | Tung |
| 5,049,591 A | 9/1991 | Hayashi et al. |
| 5,050,742 A | 9/1991 | Muckenfuhs |
| 5,054,619 A | 10/1991 | Muckenfuhs |
| 5,062,840 A | 11/1991 | Holt et al. |
| 5,085,654 A | 2/1992 | Buell |
| 5,089,558 A | 2/1992 | Hall et al. |
| 5,092,861 A | 3/1992 | Nomura et al. |
| 5,093,384 A | 3/1992 | Hayashi et al. |
| 5,098,776 A | 3/1992 | Kobayashi et al. |
| 5,114,781 A | 5/1992 | Morman |
| 5,116,662 A | 5/1992 | Morman |
| 5,118,762 A | 6/1992 | Chin |
| 5,135,786 A | 8/1992 | Hayashi et al. |
| 5,137,537 A | 8/1992 | Herron et al. |
| 5,139,832 A | 8/1992 | Hayashi et al. |
| 5,145,935 A | 9/1992 | Hayashi |
| 5,147,345 A | 9/1992 | Young et al. |
| 5,149,741 A | 9/1992 | Alper et al. |
| 5,151,092 A | 9/1992 | Buell et al. |
| 5,156,793 A | 10/1992 | Buell et al. |
| 5,156,911 A | 10/1992 | Stewart |
| 5,159,022 A | 10/1992 | Ikematu et al. |
| 5,167,897 A | 12/1992 | Weber et al. |
| 5,171,236 A | 12/1992 | Dreier et al. |
| 5,188,627 A | 2/1993 | Igaue et al. |
| 5,189,110 A | 2/1993 | Ikematu et al. |
| 5,192,301 A | 3/1993 | Kamiya et al. |
| 5,221,274 A | 6/1993 | Buell et al. |
| 5,226,992 A | 7/1993 | Morman |
| 5,234,999 A | 8/1993 | Tung et al. |
| 5,242,436 A | 9/1993 | Weil et al. |
| 5,246,433 A | 9/1993 | Hasse et al. |
| 5,256,736 A | 10/1993 | Trepka et al. |
| 5,260,345 A | 11/1993 | DesMarais et al. |
| 5,269,755 A | 12/1993 | Bodicky |
| 5,270,388 A | 12/1993 | Onishi et al. |
| 5,296,184 A | 3/1994 | Wu |
| 5,306,266 A | 4/1994 | Freeland |
| 5,336,545 A | 8/1994 | Morman |
| 5,342,338 A | 8/1994 | Roe |
| 5,344,691 A | 9/1994 | Hanschen et al. |
| 5,358,500 A | 10/1994 | Lavon et al. |
| 5,358,783 A | 10/1994 | Diehl et al. |
| 5,387,207 A | 2/1995 | Dyer et al. |
| 5,387,450 A | 2/1995 | Stewart |
| 5,397,316 A | 3/1995 | LaVon et al. |
| 5,397,318 A | 3/1995 | Dreier |
| 5,429,856 A | 7/1995 | Krueger et al. |
| 5,439,459 A | 8/1995 | Tanji et al. |
| 5,439,966 A | 8/1995 | Graham et al. |
| 5,445,140 A | 8/1995 | Tovey |
| 5,447,508 A | 9/1995 | Numano et al. |
| 5,468,237 A | 11/1995 | Miller et al. |
| 5,468,428 A | 11/1995 | Hanschen et al. |
| 5,492,751 A | 2/1996 | Butt, Sr. et al. |
| 5,499,978 A | 3/1996 | Buell et al. |
| 5,506,300 A | 4/1996 | Ward et al. |
| 5,507,736 A | 4/1996 | Clear et al. |
| 5,514,121 A | 5/1996 | Roe et al. |
| 5,518,433 A | 5/1996 | Sneddon |
| 5,518,801 A | 5/1996 | Chappell et al. |
| 5,536,563 A | 7/1996 | Shah et al. |
| 5,540,671 A | 7/1996 | Dreier |
| 5,540,976 A | 7/1996 | Shawver et al. |
| 5,545,690 A | 8/1996 | Trepka et al. |
| 5,554,142 A | 9/1996 | Dreier et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| H1630 H | 1/1997 | Roe et al. |
| 5,591,152 A | 1/1997 | Buell et al. |
| 5,607,760 A | 3/1997 | Roe |
| 5,609,587 A | 3/1997 | Roe |
| 5,620,780 A | 4/1997 | Krueger et al. |
| 5,625,222 A | 4/1997 | Yoneda et al. |
| 5,634,913 A | 6/1997 | Stinger |
| 5,635,191 A | 6/1997 | Roe et al. |
| H1670 H | 7/1997 | Aziz et al. |
| 5,643,588 A | 7/1997 | Roe et al. |
| 5,648,167 A | 7/1997 | Peck |

| | | | | | | |
|---|---|---|---|---|---|---|
| 5,653,703 | A | 8/1997 | Roe et al. | 6,598,637 | B2 | 7/2003 | Lechtenböhmer et al. |
| 5,669,897 | A | 9/1997 | LaVon et al. | 6,626,879 | B1 | 9/2003 | Ashton et al. |
| 5,691,034 | A | 11/1997 | Krueger et al. | 6,627,673 | B2 | 9/2003 | Topolkaraev et al. |
| 5,714,548 | A | 2/1998 | Ma et al. | 6,635,041 | B1 | 10/2003 | Popp et al. |
| 5,719,226 | A | 2/1998 | Kegley | 6,648,869 | B1 | 11/2003 | Schlinz et al. |
| H1732 | H | 6/1998 | Johnson | 6,657,000 | B1 | 12/2003 | De Keyzer et al. |
| 5,762,641 | A | 6/1998 | Bewick-Sonntag et al. | 6,664,309 | B2 | 12/2003 | Svenningsen et al. |
| 5,814,705 | A | 9/1998 | Ward et al. | 6,664,436 | B2 | 12/2003 | Topolkaraev et al. |
| 5,830,203 | A | 11/1998 | Sukuzi et al. | 6,673,857 | B1 | 1/2004 | Knoll et al. |
| 5,853,864 | A | 12/1998 | Bunnelle | H2100 | H | 4/2004 | Hansen et al. |
| 5,858,150 | A | 1/1999 | Yarusso et al. | 6,722,910 | B2 | 4/2004 | Kajinuma |
| 5,865,823 | A | 2/1999 | Curro | 6,746,433 | B1 | 6/2004 | Shimoe et al. |
| 5,889,118 | A | 3/1999 | Delgado et al. | 6,759,454 | B2 | 7/2004 | Stephens et al. |
| 5,897,545 | A | 4/1999 | Kline et al. | 6,759,481 | B2 | 7/2004 | Tong |
| 5,899,895 | A | 5/1999 | Robles et al. | 6,790,911 | B2 | 9/2004 | Perevosnik et al. |
| 5,910,546 | A | 6/1999 | Trepka et al. | 6,818,093 | B1 | 11/2004 | Taal et al. |
| 5,916,206 | A | 6/1999 | Otsubo et al. | 6,827,806 | B2 | 12/2004 | Uitenbroek et al. |
| 5,934,470 | A | 8/1999 | Bauer et al. | 6,844,383 | B2 | 1/2005 | Hoshi et al. |
| 5,938,648 | A | 8/1999 | LaVon et al. | 6,887,916 | B2 | 5/2005 | Zhou et al. |
| 5,941,864 | A | 8/1999 | Roe | 6,933,421 | B2 | 8/2005 | Topolkaraev et al. |
| 5,957,908 | A | 9/1999 | Kline et al. | 6,939,906 | B2 | 9/2005 | Hoshi et al. |
| 5,968,025 | A | 10/1999 | Roe et al. | 6,946,172 | B2 | 9/2005 | Munn et al. |
| 5,972,519 | A | 10/1999 | Niessner et al. | 6,967,178 | B2 | 11/2005 | Zhou et al. |
| 5,977,430 | A | 11/1999 | Roe et al. | 6,969,441 | B2 | 11/2005 | Welch et al. |
| 5,997,520 | A | 12/1999 | Ahr et al. | 6,978,486 | B2 | 12/2005 | Zhou et al. |
| 6,004,306 | A | 12/1999 | Robles et al. | 7,015,155 | B2 | 3/2006 | Zhou et al. |
| 6,010,490 | A | 1/2000 | Freeland et al. | 7,056,411 | B2 | 6/2006 | Desai et al. |
| 6,013,063 | A | 1/2000 | Roe et al. | 7,074,484 | B2 | 7/2006 | Topolkaraev et al. |
| 6,025,071 | A | 2/2000 | Cameron et al. | 7,087,287 | B2 | 8/2006 | Curro et al. |
| 6,031,053 | A | 2/2000 | Knoll et al. | 7,223,261 | B2 | 5/2007 | Müeller et al. |
| 6,063,838 | A | 5/2000 | Patnode et al. | 7,316,840 | B2 | 1/2008 | Neculescz et al. |
| 6,103,814 | A | 8/2000 | Vandrongelen et al. | 7,316,842 | B2 | 1/2008 | Zhou et al. |
| 6,107,537 | A | 8/2000 | Elder et al. | 2001/0004689 | A1 | 6/2001 | Otsubo |
| 6,120,487 | A | 9/2000 | Ashton | 2002/0056384 | A1 | 5/2002 | Fujimoto et al. |
| 6,120,489 | A | 9/2000 | Johnson et al. | 2002/0096072 | A1 | 7/2002 | Fujimoto et al. |
| 6,120,866 | A | 9/2000 | Arakawa et al. | 2002/0115744 | A1 | 8/2002 | Svenningsen et al. |
| 6,140,433 | A | 10/2000 | Zhang et al. | 2002/0115772 | A1 | 8/2002 | Topolkaraev et al. |
| 6,149,637 | A | 11/2000 | Allen et al. | 2002/0115977 | A1 | 8/2002 | Topolkaraev et al. |
| 6,156,842 | A | 12/2000 | Hoenig et al. | 2002/0143313 | A1 | 10/2002 | Tsuji et al. |
| 6,168,584 | B1 | 1/2001 | Allen et al. | 2002/0147273 | A1 | 10/2002 | Patel et al. |
| 6,177,517 | B1 | 1/2001 | Guntherberg et al. | 2002/0165516 | A1 | 11/2002 | Datta et al. |
| 6,179,820 | B1 | 1/2001 | Fernfors | 2003/0088228 | A1 | 5/2003 | Desai et al. |
| 6,184,285 | B1 | 2/2001 | Goodman et al. | 2003/0091807 | A1 | 5/2003 | Desai et al. |
| 6,187,696 | B1 | 2/2001 | Lim et al. | 2003/0111166 | A1 | 6/2003 | Uitenbroek et al. |
| 6,190,768 | B1 | 2/2001 | Turley et al. | 2003/0120240 | A1 | 6/2003 | Buell et al. |
| 6,193,701 | B1 | 2/2001 | Van Gompel et al. | 2003/0233082 | A1 | 12/2003 | Kline et al. |
| 6,194,073 | B1 | 2/2001 | Li et al. | 2004/0005832 | A1 | 1/2004 | Zhou et al. |
| 6,197,889 | B1 | 3/2001 | Knoll et al. | 2004/0005834 | A1 | 1/2004 | Zhou et al. |
| 6,211,272 | B1 | 4/2001 | Hansen et al. | 2004/0005835 | A1 | 1/2004 | Zhou et al. |
| 6,235,847 | B1 | 5/2001 | Hoshi et al. | 2004/0006324 | A1 | 1/2004 | Zhou et al. |
| 6,245,050 | B1 | 6/2001 | Odorzynski et al. | 2004/0013852 | A1 | 1/2004 | Curro et al. |
| 6,265,484 | B1 | 7/2001 | Trepka et al. | 2004/0092900 | A1 | 5/2004 | Hoffman et al. |
| 6,265,485 | B1 | 7/2001 | Trepka et al. | 2004/0092902 | A1 | 5/2004 | Hoffman |
| 6,274,666 | B1 | 8/2001 | Dougherty | 2004/0123938 | A1 | 7/2004 | Zhou et al. |
| 6,274,685 | B2 | 8/2001 | Blok et al. | 2004/0127881 | A1 | 7/2004 | Stevens et al. |
| 6,288,149 | B1 | 9/2001 | Kroll | 2004/0162536 | A1 | 8/2004 | Becker |
| 6,300,208 | B1 | 10/2001 | Talwar et al. | 2004/0162538 | A1 | 8/2004 | Mueller |
| 6,310,154 | B1 | 10/2001 | Babcock et al. | 2004/0167486 | A1 | 8/2004 | Busam |
| 6,357,499 | B1 | 3/2002 | Kralevich, Jr. et al. | 2004/0181200 | A1 | 9/2004 | Desai et al. |
| 6,369,160 | B1 | 4/2002 | Knoll et al. | 2004/0182499 | A1 | 9/2004 | Zhou et al. |
| 6,372,853 | B1 | 4/2002 | Li et al. | 2004/0193134 | A1 | 9/2004 | Mueller et al. |
| 6,383,431 | B1 | 5/2002 | Dobrin et al. | 2004/0222553 | A1 | 11/2004 | Desai et al. |
| 6,418,848 | B1 | 7/2002 | Fujimoto et al. | 2005/0095942 | A1 | 5/2005 | Mueller |
| 6,419,798 | B1 | 7/2002 | Topolkaraev et al. | 2005/0096416 | A1 | 5/2005 | Zhou et al. |
| 6,423,807 | B1 | 7/2002 | Oi et al. | 2005/0170729 | A1 | 8/2005 | Stadelman et al. |
| 6,432,098 | B1 | 8/2002 | Kline et al. | 2005/0171499 | A1 | 8/2005 | Nigam et al. |
| 6,444,755 | B1 | 9/2002 | DePorter et al. | 2005/0177123 | A1 | 8/2005 | Catalan |
| 6,455,627 | B1 | 9/2002 | De Keyzer et al. | 2005/0211368 | A1 | 9/2005 | McGuire |
| 6,476,288 | B1 | 11/2002 | Vanrijswijck et al. | 2005/0215963 | A1 | 9/2005 | Autran et al. |
| 6,482,191 | B1 | 11/2002 | Roe et al. | 2005/0215972 | A1 | 9/2005 | Roe et al. |
| 6,485,557 | B1 | 11/2002 | Swiler | 2005/0215973 | A1 | 9/2005 | Roe et al. |
| 6,521,704 | B1 | 2/2003 | Hubbard et al. | 2005/0256476 | A1 | 11/2005 | Mirle et al. |
| 6,531,544 | B1 | 3/2003 | Vaughan et al. | 2005/0273071 | A1 | 12/2005 | McKiernan et al. |
| 6,533,987 | B2 | 3/2003 | Topolkaraev et al. | 2005/0273072 | A1 | 12/2005 | Hird et al. |
| 6,565,549 | B1 | 5/2003 | Allen et al. | 2006/0003656 | A1 | 1/2006 | Morman |
| 6,571,704 | B2 | 6/2003 | Fujimoto et al. | 2006/0004342 | A1 | 1/2006 | Sawyer et al. |
| 6,579,940 | B1 | 6/2003 | Dove | 2006/0058765 | A1 | 3/2006 | Mueller |
| 6,592,995 | B2 | 7/2003 | Topolkaraev et al. | 2006/0078042 | A1 | 4/2006 | Lee |
| 6,593,430 | B1 | 7/2003 | Knoll et al. | 2006/0083900 | A1 | 4/2006 | Ashraf |

| | | | |
|---|---|---|---|
| 2006/0155255 A1 | 7/2006 | Mckiernan et al. | |
| 2006/0167434 A1 | 7/2006 | Ashton et al. | |
| 2006/0264858 A1 | 11/2006 | Roe et al. | |
| 2007/0037907 A9 | 2/2007 | Zhou et al. | |
| 2007/0088307 A1 | 4/2007 | Arizti | |
| 2007/0093771 A1 | 4/2007 | Arizti | |
| 2007/0191806 A1 | 8/2007 | Mueller | |
| 2007/0197993 A1 | 8/2007 | Arizti | |
| 2007/0197994 A1 | 8/2007 | Arizti | |
| 2008/0033388 A1 | 2/2008 | Mueller | |
| 2008/0108963 A1 | 5/2008 | Ashton et al. | |
| 2008/0195070 A1 | 8/2008 | Ponomarenko | |

FOREIGN PATENT DOCUMENTS

| | | |
|---|---|---|
| DE | 1910911 | 3/1969 |
| EP | 0119827 | 7/1988 |
| EP | 0316671 | 11/1988 |
| EP | 0433951 | 6/1991 |
| EP | 0591647 | 4/1994 |
| EP | 0597331 | 5/1994 |
| EP | 0451919 | 2/1995 |
| EP | 0650714 | 5/1995 |
| EP | 0703068 | 3/1996 |
| EP | 0847738 | 6/1998 |
| EP | 1351815 | 2/2005 |
| EP | 1013291 | 6/2005 |
| EP | 1226018 | 10/2005 |
| GB | 2297473 | 8/1995 |
| GB | 2287888 | 10/1995 |
| GB | 2328158 | 2/1999 |
| GB | 2329842 | 4/1999 |
| JP | 62241944 | 10/1987 |
| JP | 63238153 | 10/1988 |
| JP | 3160083 | 7/1991 |
| JP | 3160084 | 7/1991 |
| JP | 3239738 | 10/1991 |
| JP | 4153288 | 5/1992 |
| JP | 7157738 | 6/1995 |
| JP | 8060120 | 3/1996 |
| JP | 8060121 | 3/1996 |
| JP | 8277382 | 10/1996 |
| JP | 8281764 | 10/1996 |
| JP | 9291265 | 11/1997 |
| JP | 9302319 | 11/1997 |
| JP | 2000282006 | 5/1999 |
| JP | 11279521 | 10/1999 |
| JP | 2001040302 | 2/2001 |
| JP | 2001279212 | 10/2001 |
| JP | 2001293789 | 10/2001 |
| WO | WO 94/14395 | 7/1994 |
| WO | WO 95/16746 | 6/1995 |
| WO | WO 96/11236 | 4/1996 |
| WO | WO 96/23823 | 8/1996 |
| WO | WO 98/08476 | 3/1998 |
| WO | WO 99/13016 | 3/1999 |
| WO | WO 00/12645 | 3/2000 |
| WO | WO 00/22061 | 4/2000 |
| WO | WO 00/30581 | 6/2000 |
| WO | WO 00/69834 | 11/2000 |
| WO | WO 01/87589 | 11/2001 |
| WO | WO 02/083786 | 10/2002 |
| WO | WO 03/047488 | 6/2003 |
| WO | WO 03/082571 | 10/2003 |
| WO | WO 2006/074481 | 7/2006 |

OTHER PUBLICATIONS

Ziabicki, *Fundamentals of Fibre Formation*, John Wiley & Sons, New York (1976), Chapter 6.

J.H. Briston, *Plastic Films*, 2$^{nd}$ Edition, Longman Inc., New York (1983), pp. 83-85.

I.M. Ward, *Mechanical Properties of Solid Polymers*, Wiley-Interscience, New York (1971), p. 278.

U.S. Appl. No. 11/144,508, filed Jun. 3, 2005, Herd et al., Office Action dated Mar. 16, 2009.

U.S. Appl. No. 11/144,508, filed Jun. 3, 2005, Herd et al., Office Action dated Jul. 16, 2008.

U.S. Appl. No. 11/144,508, filed Jun. 3, 2005 Herd et al., Office Action dated May 18, 2007.

U.S. Appl. No. 11/145,353, filed Jun. 3, 2005, McKiernan et al., Office Action dated Feb. 10, 2009.

U.S. Appl. No. 11/145,353, filed Jun. 3, 2005, McKiernan et al., Office Action dated Jul. 30, 2008.

U.S. Appl. No. 11/145,353, filed Jun. 3, 2005, McKiernan et al., Office Action dated Dec. 11, 2007.

U.S. Appl. No. 11/340,803, filed Jan. 26, 2006, Ashton et al., Office Action dated Apr. 7, 2009.

U.S. Appl. No. 11/340,803, filed Jan. 26, 2006, Ashton et al., Office Action dated Dec. 16, 2008.

U.S. Appl. No. 11/340,803, filed Jan. 26, 2006, Ashton et al., Office Action dated Jun. 18, 2008.

U.S. Appl. No. 11/144,497, filed Jun. 3, 2005, McKiernan et al., Office Action dated Jan. 22, 2009.

U.S. Appl. No. 11/144,497, filed Jun. 3, 2005, McKiernan et al., Office Action dated May 1, 2008.

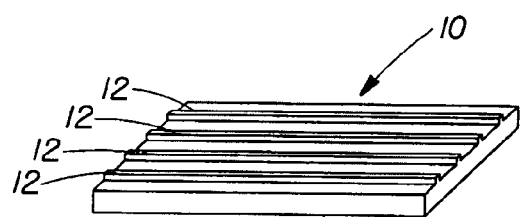
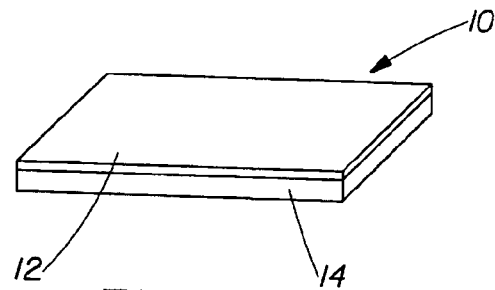
Fig. 1A  Fig. 1B
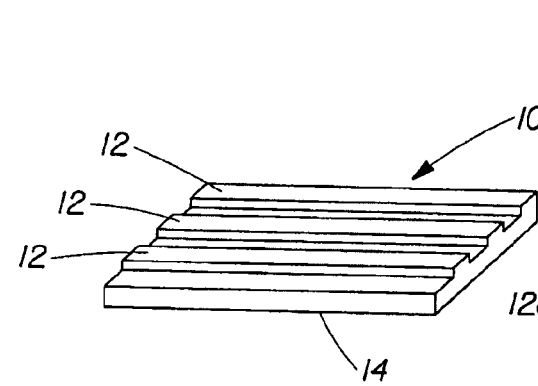
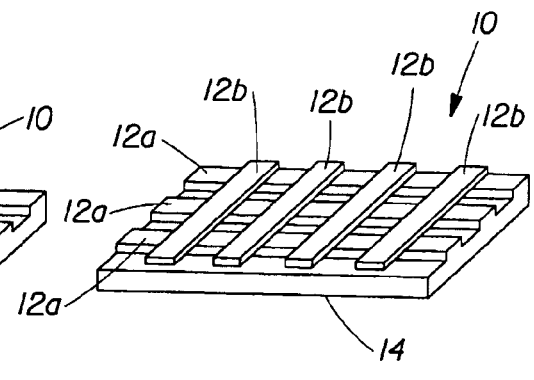
Fig. 1C  Fig. 1D
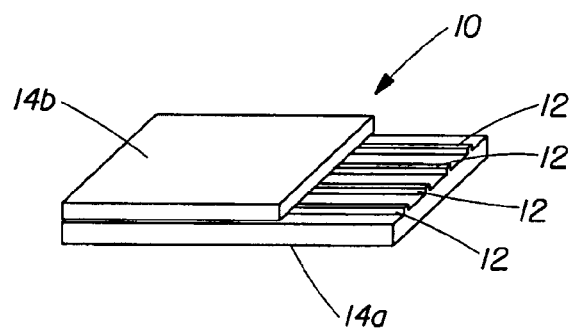
Fig. 1E

ABSORBENT ARTICLES COMPRISING A SLOW RECOVERY STRETCH LAMINATE AND METHOD FOR MAKING THE SAME

CROSS REFERENCE TO RELATED APPLICATION

This application claims the benefit of U.S. Provisional Application No. 61/003,954, filed Nov. 21, 2007, the substance of which is incorporated herein by reference.

FIELD OF THE INVENTION

This invention is directed to absorbent articles such as diapers, training pants, adult incontinence articles, feminine hygiene articles, and the like comprising a slow recovery stretch laminate and a method for making the slow recovery stretch laminate.

BACKGROUND OF THE INVENTION

Stretch laminates are well known in the art. It has long been known in the field of disposable absorbent articles that it is desirable to construct absorptive devices, such as disposable diapers with fasteners, pull-on diapers, training pants, sanitary napkins, pantiliners, incontinence briefs, and the like, with stretch laminates to improve the ease of motion and maintenance of a sustained fit. Furthermore, stretch laminates allow the diaper to accommodate a range of different sized wearers. A diaper may have stretch laminates in a number of its article elements including the waist band, leg cuffs, side panels, elasticized topsheets, backsheet, ears, outercover, and fastening system.

During application, a diaper generally may be stretched and elongated longitudinally and/or laterally from its initial substantially compacted and untensioned state. Upon release of the elongating tension, the diaper often contracts, constricts, and/or folds before it can be successfully applied to or adjusted on a wearer. In traditional taped diapers, the stretch laminates, which may be present in a leg cuff, may require elongation prior to application onto a wearer. However, if a continuous force is not maintained, the stretch laminates within the leg cuff may cause the diaper to retract quickly. Generally, a caregiver needs to apply a continuous elongating force to the diaper while at the same time positioning the diaper onto the wearer and tending to the wearer who may be uncooperative (e.g., crying, fussing, moving, resisting, etc.) during the diapering process. These multiple simultaneous requirements can lead to frustration for the caregiver. The multiple simultaneous requirements may result in the diaper being positioned improperly on the wearer.

Similarly, in pant-type articles, the stretch laminates, which may be present in a waist feature, side panel, leg band or outer cover, may require elongation so as to enlarge the waist opening from an initial constrictive and untensioned state. A continuous force may need to be applied during the application process, generally by a caregiver or wearer, to counteract the rapid retraction of the stretch laminates that would be experienced otherwise. Leg openings in pants-type articles commonly incorporate stretch laminates and may also tend to retract quickly thereby increasing the difficulty of pulling the article up to the desired location on the wearer's lower torso. Applying a continuous force to maintain an enlarged waist opening may be difficult for young children who lack the hand strength and dexterity to apply the continuous force while simultaneously pulling on the pant. Likewise, elderly individuals may also lack the necessary hand strength and dexterity to apply a continuous force while simultaneously pulling on an incontinence article.

Furthermore, recent diaper advancements have focused on the acceptance and storage of feces. In conventional diaper designs, feces remain between the diaper's topsheet and the wearer's skin. As a result, the wearer experiences excessive soiling, irritation, and the potential of leakage generally around the leg cuff. Advances in diaper design include the use of an apertured elasticized topsheet to isolate feces away from the wearer's skin thus preventing leakage and irritation. The apertured elasticized topsheet forms a void between the elasticized topsheet and the underlying diaper structure. A stretch laminate generally is associated with the elasticized topsheet to aid in keeping the elasticized topsheet substantially in contact with the wearer's skin. Furthermore, the stretch laminate aids in keeping the aperture positioned so that the underlying diaper structure may receive the fecal insult. Examples of elasticized topsheets may be found in U.S. Pub. Nos. 2005-0273071, 2005-0171499, 2007-0191806, 2004-0162538, and 2005-0095942.

While elasticized topsheets are conceptually advantageous, diapers with elasticized topsheets comprising conventional elastomers are often difficult to apply. Application of the diaper requires a caregiver to stretch the diaper so that it is in a substantially planar position. Upon release, the stretch laminate contracts at a rate that makes it difficult for the caregiver to position the diaper correctly onto the wearer. This "snap-back" of the elasticized topsheet may increase the difficulty of applying the diaper to the wearer. If the diaper is difficult to apply, there may be a tendency for mispositioning the aperture, which may result in fecal deposit on the elasticized topsheet rather than through the aperture. Mispositioning of the aperture can destroy the benefit of isolating feces from the wearer's skin. Examples of diapers comprising an elasticized topsheet having an aperture have been disclosed in U.S. Pat. No. 4,892,536, issued to Des Marais et al. and U.S. Pat. No. 4,990,147 issued to Freeland.

Thus, there is a need for an absorbent product comprising a stretch laminate that retracts slowly upon being released from a stretched state, thus facilitating application and positioning of the product correctly onto the wearer.

One problem that exists in filling the need for a stretch laminate that retracts slowly upon release from a stretched state is that stretch laminates are an amalgam of materials. Stretch laminates generally may include an elastic member and a relatively inelastic substrate. The elastic member and the substrate may be joined by bonding techniques known in the art such as by an adhesive. It is the combination of these materials as a laminate that must result in the slow recovery. Furthermore, the formation technique can affect the recovery characteristics of the resultant stretch laminate. For example, a stretch bonded laminate involves joining a strained elastic member to a substantially inelastic substrate. Upon release of the strain force, the elastic member retracts and may gather the substrate. The initial strain of the elastic member can impact the extendibility and the recovery characteristic of the stretch laminate. The construction and basis weight of the substrate may also impact the recovery characteristic of the stretch laminate.

Another problem that exists in filling the need for a slow recovery stretch laminate is that during the manufacture of said stretch laminate, the elastic member should be strained relatively uniformly in order for the laminate to have consistent properties and thereby provide reliable performance for the end user. Additionally, for economic reasons, it is advantageous to fabricate the stretch laminate in a high line speed continuous process, which in turn further complicates the manufacture of a slow recovery stretch laminate with reliable performance. This additional complication is primarily a result of the higher characteristic strain rates the elastic member experiences at high line speeds. For a given stretch lamination process and operating temperature, as line speed is increased, the strain rate increases, and higher strain rates more readily give rise to stability problems in the stretching process.

SUMMARY OF THE INVENTION

In response to the problems identified above, the present invention provides an absorbent article comprising a topsheet, a backsheet joined with the topsheet, an absorbent core interposed between the topsheet and backsheet; and a slow recovery stretch laminate. Further, the present invention also provides for a reliable slow recovery stretch laminate manufactured in a continuous process. The slow recovery stretch laminate of an absorbent article element may exhibit an unload force at 37° C. of about 0.16 N/(g/m) or greater and a percent of initial strain after 15 seconds of recovery at 22° C. of about 10% or greater. The slow recovery stretch laminate may comprise an elastic member that is pretreated by one or a combination of preheating, prestretching, and incremental stretching prior to and/or during draw down of the elastic member. Additionally, the elastic member may exhibit one or more of the following: (i) a yield stress drop of about 0.3 MPa or less at the characteristic strain rate and characteristic temperature of the stretching process, (ii) a percent yield stress drop of about 30 percent or less at the characteristic strain rate and characteristic temperature of the stretching process, (iii) a yield stress drop of about 0.15 MPa or less at the initial tensile strain rate equal to the characteristic strain rate of the stretching process and at the characteristic temperature of the stretching process, and (iv) a percent yield stress drop of about 20 percent or less at the initial tensile strain rate equal to the characteristic strain rate of the stretching process and at the characteristic temperature of the stretching process.

Further, the present invention may provide for a plurality of absorbent articles contained within the package, where each absorbent article in the package comprises a topsheet, a backsheet joined with the topsheet, an absorbent core interposed between the topsheet and backsheet, and an article element. At least one article element for each absorbent article in the package may comprise a slow recovery stretch laminate exhibiting an unload force at 37° C. of about 0.16 N/(g/m) or greater and a percent of initial strain after 15 seconds of recovery at 22° C. of about 10% or greater. The slow recovery stretch laminate may exhibit a percent coefficient of variation of less than about 15% for the unload force at 37° C. and a percent coefficient of variation of less than about 15% for the initial strain after 15 seconds of recovery at 22° C.

BRIEF DESCRIPTION OF THE DRAWINGS

FIGS. 1A-E are perspective views of embodiments of the slow recovery stretch laminate.

DETAILED DESCRIPTION OF THE PRESENT INVENTIONS

Figure 2:
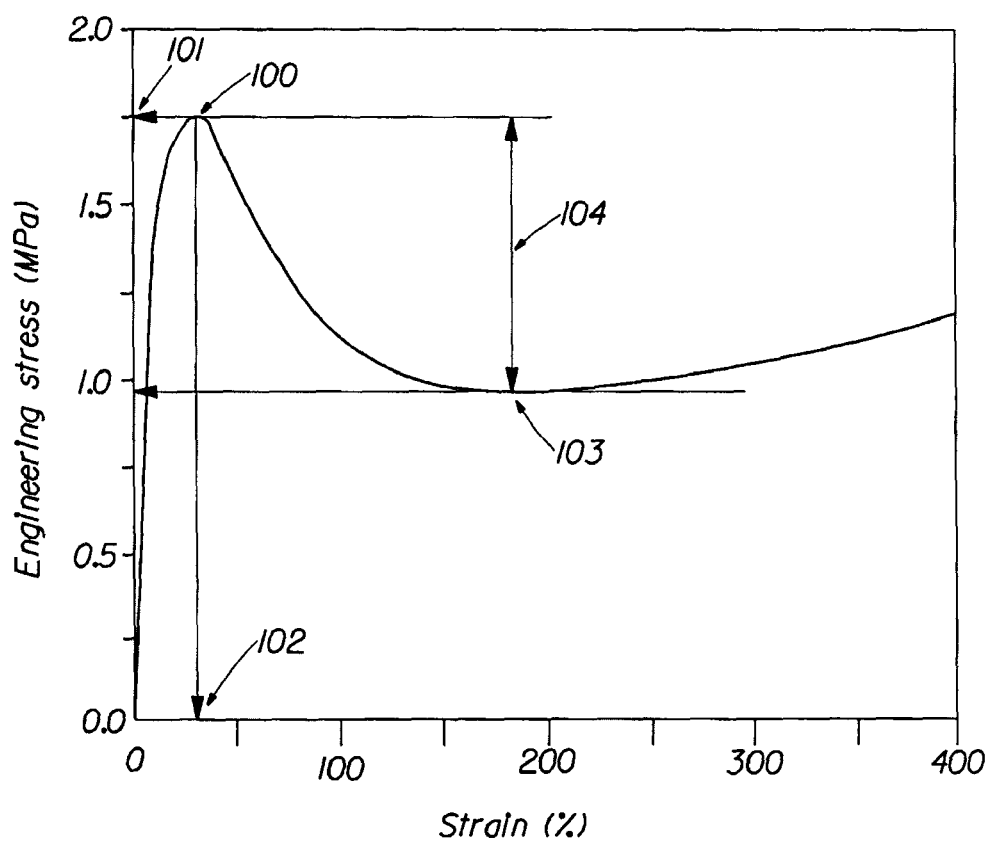
FIG. 2 is an example engineering stress-strain curve for a material that exhibits a yield drop.

As used herein, the term "absorbent article" or "article" refers to a wearable device that absorbs and/or contains liquid and, more specifically, refers to a device that is placed against or in proximity to the body of the wearer to absorb and contain the various exudates discharged from the body. Suitable examples include diapers, training pants, pull-on garments, adult incontinence products and feminine care products such as sanitary napkins. Furthermore, "absorbent article" includes "disposable absorbent article" which is intended to be discarded and not laundered or otherwise restored after no more than ten uses, preferably after no more than five uses, and most preferably after a single use (although certain components may be recycled, reused, or composted).

As used herein, the term "stretch laminate" generally refers to an elastomer which is attached to at least one material such as a polymeric film, a nonwoven, a woven, or a scrim. The elastomer may be attached to the material by any of a number of bonding methods known to those skilled in the art, including adhesive bonding, thermal bonding, pressure bonding, ultrasonic bonding, and the like, or any combination thereof.

As used herein, the term "laminate" refers to a material comprising two or more layers. The term includes stretch laminates and non-stretch laminates.

As used herein, the term "diaper" refers to an absorbent article generally worn by infants and incontinent persons about the lower torso.

As used herein, the term "substrate" refers to a material that is laminated to the elastic member to form the stretch laminate. Suitable substrates include nonwoven webs, woven webs, knitted fabrics, films, film laminates, apertured films, nonwoven laminates, sponges, foams, scrims, and any combinations thereof. Suitable substrates may comprise natural materials, synthetic materials, or any combination thereof.

As used herein, the term "longitudinal" generally means a direction running parallel to the longitudinal axis, of the article and includes directions within 45° of the longitudinal direction.

As used herein, the term "length" of the article or component thereof generally refers to the size/distance of the maximum linear dimension, or typically to the size/distance of the longitudinal axis, or an article or part thereof.

As used herein, the terms "lateral" or "transverse" refer to a direction generally orthogonal to the longitudinal direction and parallel to the transverse axis.

As used herein, the term "width" of the article or of a component thereof refers to the size/distance of the dimension orthogonal to the longitudinal direction of the article or component thereof, e.g. orthogonal to the length of the article or component thereof, and typically it refers to the distance/size of the dimension parallel to the transverse axis of the article or component.

As used herein, the term "attached" encompasses configurations whereby an element is directly secured to another element by affixing the element directly to the other element.

As used herein, the term "joined" or "connected" encompasses configurations whereby a first element is directly secured to second element by affixing the first element directly to the second element and configurations whereby a first element is indirectly secured to a second element by affixing the first element to intermediate member(s), which in turn are affixed to the second element. "Joined" or "connected" elements may be affixed either continuously or intermittently.

As used herein, "relaxed" or "relaxed state" means the state where no forces are applied to an article (other than naturally occurring forces such as gravity).

As used herein, the terms "extendibility" and "extensible", e.g. extendibility of the elastomer, mean that the width or length of the item in the relaxed position can be extended or increased.

As used herein, "elasticated" or "elasticized" means that the component comprises at least a portion made of elastic material.

As used herein, the terms "elastic," "elastomer," and "elastomeric" refer to a material which generally is able to extend to a strain of at least 50% without breaking or rupturing, and is able to recover substantially to its original dimensions after the deforming force has been removed.

As used herein, the term "medical product" means surgical gowns and drapes, face masks, head coverings, shoe coverings, wound dressings, bandages and sterilization wraps as disclosed in U.S. Pat. No. 5,540,976.

As used herein, the term "copolymer" refers to a polymer synthesized from two or more monomers with different chemical structures.

As used herein, the terms "temperature responsive" and "temperature responsiveness" refer to a slow recovery stretch laminate exhibiting less post elongation strain after a specified amount of time at higher temperatures than at lower temperatures.

As used herein, the term "conventional stretch laminate" refers to a stretch laminate that exhibits a minimal percent of initial strain after 15 seconds of recovery at 22° C. as measured by the Post Elongation Recovery Test. Conventional stretch laminates exhibit a percent of initial strain after 15 seconds of recovery at 22° C. of less than 10%, as measured by the Post Elongation Recovery Test.

As used herein, the term "percent of initial strain remaining" refers to the percentage of initial strain remaining after some period of time after release from that initial strain as measured by the Post Elongation Recovery Test. "Percent of initial strain remaining" is calculated by dividing the percent strain at a given time after release from an initial strain by the initial percent strain; the quotient is multiplied by 100 to yield a percentage.

As used herein, the terms "stress", "engineering stress", and "nominal stress" refer to the load divided by the initial undeformed cross-sectional area of the sample on which a deformation force acts.

As used herein, the terms "strain" and "engineering strain" refer to the change in sample length divided by the initial undeformed length of the sample on which a deformation force acts, usually expressed as a percent.

As used herein, the term "yield point" refers to the point on a engineering stress versus strain curve beyond which deformation is not completely recoverable, the term "yield stress" refers to the engineering stress value at the yield point, and the term "yield strain" refers to the level of strain at the yield point usually expressed as a percent strain. Some materials may also exhibit a "yield drop", i.e., a decrease in engineering stress with increasing strain.

As used herein, for materials exhibiting a yield drop, the term "post yield minimum stress" refers to the lowest stress value on an engineering stress versus strain curve located between the yield strain and the strain at break or failure.

As used herein, for materials exhibiting a yield drop, the term "yield stress drop" refers to the value of the yield stress minus the value of the post yield minimum stress. The term "percent yield stress drop" refers to the ratio of the yield stress drop to the yield stress multiplied by 100.

As used herein, the terms "strain at break", "strain at failure", and "ultimate strain" refer to the maximum tensile strain to which a material can be subjected before it breaks, and is often expressed as the percentage strain.

As used herein, the term "reliable" refers to a low coefficient of variation for each property of interest (e.g., a low coefficient of variation of the unload force at 37° C. as measured by the Two Cycle Hysteresis Test described below or a low coefficient of variation of the percent of the initial strain after 15 seconds of recovery at 22° C. as measured by the Post Elongation Recovery Test described below) in a given article element (e.g., an anal cuff, an elasticized topsheet, a fastening system, a leg cuff, a waist elastic feature, a side panel, an ear, an outer cover, etc.) comprising a slow recovery stretch laminate (SRSL) manufactured in a continuous process. The coefficient of variation expressed as a percentage (i.e., a percent coefficient of variation) refers to the ratio of the standard deviation to the arithmetic average multiplied by 100. For various reasons, it may be desirable to keep this value below about 15% or about 10% for each property of interest. Thus, when an article element in an absorbent article comprises a SRSL, it may be desirable to keep the percent coefficient of variation below about 15% or about 10% for both the unload force at 37° C. and the initial strain after 15 seconds of recovery at 22° C. of the SRSL; where each percent coefficient of variation is based on the arithmetic average and standard deviation obtained from measurements of five SRSLs taken from the identical position on each of five randomly chosen absorbent articles contained within one or more kits (e.g., a consumer-sized package of taped diapers, a consumer-sized package of pull-on diaper pants, a consumer-sized package of feminine hygiene pads of substantially identical absorbent articles). In those instances where there are five or more absorbent articles per kit, the percent coefficient of variation of the unload force at 37° C. and the percent coefficient of variation of the initial strain after 15 seconds of recovery at 22° C. should be determined from the five SRSLs taken from the identical position on each of five randomly chosen absorbent articles contained within a single kit.

When an absorbent article comprises more than one article element comprising a SRSL, the percent coefficient of variation is determined for each type of article element comprising the SRSL; and for each type of article element the percent coefficient of variation is determined for both the unload force at 37° C. and the initial strain after 15 seconds of recovery at 22° C. For each type of article element and property measure, the percent coefficient of variation is based on the arithmetic average and standard deviation obtained from measurements of five SRSLs taken from the identical position on each of five randomly chosen absorbent articles contained within one or more kits of substantially identical absorbent articles. For each type of article element comprising a SRSL, it may be desirable to keep the percent coefficient of variation below about 15% or about 10% for both the unload force at 37° C. and the initial strain after 15 seconds of recovery at 22° C. of the SRSL. For example, if an absorbent article comprises a leg cuff comprising a SRSL and an elasticized topsheet comprising a SRSL, the unload force at 37° C., the initial strain after 15 seconds of recovery at 22° C., and the percent coefficient of variation of each property are determined separately for both the leg cuff and elasticized topsheet as delineated above. For this example, four property measures and four percent coefficient of variations would be determined—(1) the unload force at 37° C. for the leg cuff, (2) the initial strain after 15 seconds of recovery at 22° C. for the leg cuff, (3) the unload force at 37° C. for the elasticized topsheet, (4) the initial strain after 15 seconds of recovery at 22° C. for the elasticized topsheet, (5) the percent coefficient of variation of the unload force at 37° C. for the leg cuff, (6) the percent coefficient of variation of the initial strain after 15 seconds of recovery at 22° C. for the leg cuff. (7) the percent coefficient of variation of the unload force at 37° C. for the elasticized topsheet, and (8) the percent coefficient of variation of the initial strain after 15 seconds of recovery at 22° C. for the elasticized topsheet.

As used herein, the term "characteristic strain rate" refers to the average strain rate the elastic member experiences during the draw down portion of the manufacturing of the SRSL.

As used herein, the term "characteristic temperature" refers to the average temperature the elastic member experiences during the draw down portion of the manufacturing of the slow recovery laminate.

As used herein, the term "draw down" refers to the stretching of the elastic member by pulling the elastic member away faster than the process feed rate. In a continuous process this is generally accomplished by using differential roll speeds to control the level of draw down as well as the characteristic strain rate.

As used herein, the term "in-line strain" refers to the percent level of strain the elastic member is stretched during draw down.

As used herein, the term "initial tensile strain rate" refers to the initial strain rate a material will experience when extended in a standard tensile test such as described in ASTM D 882. The initial tensile strain rate is equal to the rate of grip separation divided by the initial distance between grips.

As used herein, the term "tensile modulus of elasticity" or "Young's modulus" is a measure of the stiffness of a material. For thin materials (less than about 1.0 millimeter in thickness), the tensile modulus of elasticity can be determined according to ASTM D 882; while for thick materials (greater that about 1.0 millimeter and less than about 14 millimeters in thickness), the tensile modulus of elasticity can be determined according to ASTM D 638.

The absorbent article of the present invention comprises a SRSL. The SRSL may be used within the absorbent article wherever elastic properties are desired. The SRSL generally comprises an elastic member joined to a substrate. The SRSL may be formed discretely and joined with the absorbent article. Conversely, the SRSL may be integral to the absorbent article (e.g., an elastic member is joined to an existing substrate in the absorbent article such as the topsheet to form a stretch laminate). The elastic member may be prepared from a composition comprising an elastomeric polymer, optionally at least one modifying resin, and optionally one or more additives. The SRSL exhibits a normalized unload force at 37° C. of at least about 0.16 N/(g/m) as measured by the Two Cycle Hysteresis Test described below. The SRSL exhibits a percent of initial strain after 15 seconds of recovery at 22° C. of about 10% or greater, as measured by the Post Elongation Recovery Test as described below.

In another embodiment of the present invention, the SRSL may be incorporated into a medical product such as a surgical gown, a face mask, a head covering, a shoe covering, a wound dressing, a bandage, or a sterilization wrap. The SRSL may be used in the medical products at locations where an elastic character is desired.

As shown in FIGS. 1A-E, the SRSL 10 generally comprises an elastic member 12 joined to a substrate 14. Joining of the elastic member 12 and the substrate 14 may be conducted by a variety of bonding methods such as heat bonds, pressure bonds, ultrasonic bonds, mechanical bonds, adhesive bonds, or any other suitable attachment means or combinations of these attachment means as are known in the art. In certain embodiments, the elastic member 12 may exhibit sufficient tack to join the elastic member 12 and the substrate 14.

The elastic members 12 having a variety of forms may be used in the SRSL 10. Suitable forms for the elastic members 12 include, but are not limited to films, bands, strands, individualized fibers, scrims, cross-hatch arrays, foams, or combinations thereof.

FIGS. 1A-E depict several suitable embodiments of the SRSL 10. FIG. 1A depicts a SRSL 10 having one or more elastic members 12 in the form of bands or ribbons joined with a substrate 14. FIG. 1B depicts a SRSL 10 having a sheet-like elastic member 12 joined with a sheet-like substrate 14. The elastic member 12 and the substrate 14 are shown as being coterminous; however, either layer may have dimensions differing from the other layer. FIG. 1C depicts a SRSL 10 having one or more elastic members 12 in the form of strands joined with a substrate 14.

FIG. 1D depicts a SRSL 10 having one or more elastic members in the form of a cross-hatch array joined with a substrate 14. A cross-hatch array may be formed in one instance by joining a plurality of elastic members 12a in parallel to the substrate 14. A second plurality of elastic members 12b may be joined in parallel to the substrate. The second plurality 12b may be joined in a non-parallel configuration to the first plurality 12a. A cross-hatch array may also be formed by hot needle punching of an elastomeric film. A cross-hatch array may also be formed from a porous, macroscopically-expanded, three-dimensional elastomeric web as described in U.S. Patent Application Publication No. 2004/0013852. The publication describes how the cross-hatch array can be achieved by forming the film on a porous forming structure and applying a fluid pressure differential across the thickness of the film. The fluid pressure differential causes the film to conform to the supporting structure and rupture thereby creating a cross-hatch array. FIG. 1E depicts a SRSL 10 having one or more elastic members 12 joined to two or more substrates: first substrate 14a and second substrate 14b. The particular order of the SRSL 10 layers can vary; however, in the embodiment depicted, the elastic members 12 are disposed between the first substrate 14a and the second substrate 14b, and may be bonded to one or both. The first and second substrate 14a, 14b may comprise the same material or may be distinct.

Other suitable embodiments of the SRSL 10 include using the stretch zones as disclosed in co-pending U.S. application Ser. No. 11/145,353 filed on Jun. 3, 2005 in the name of McKiernan et al., which claims the benefit of U.S. Provisional Application No. 60/643,920, filed Jan. 10, 2005.

The techniques for the formation of stretch laminates are well known in the art, and these techniques may be applicable in the formation of the SRSL 10 of the present invention. One technique for creating a stretch laminate, which is commonly known as "stretch bonding," involves an elastic member such as elastic strands, bands, ribbons, films, or the like being joined to a substrate while the elastic member is in a stretched configuration. Generally, the elastic member may be stretched to at least 25% of its relaxed length. After joining, the elastic member is allowed to relax thereby gathering the substrate and creating a stretch laminate.

Another technique for creating a stretch laminate, which is commonly known as "neck bonding," involves an elastic member being bonded to a substrate while the substrate is extended and necked. In certain embodiments, the substrate may be a non-elastic substrate. Examples of neck-bonded laminates are described in U.S. Pat. Nos. 5,226,992; 4,981, 747; 4,965,122; and 5,336,545. A variant of "neck bonding" is "neck stretch bonding." Neck stretch bonding refers to an elastic member being bonded to a substrate while the substrate is extended and necked and the elastic member extended. Examples of necked stretch bonded laminates are described in U.S. Pat. Nos. 5,114,781 and 5,116,662.

In another technique for forming a stretch laminate, elastic members can be attached to a substrate in either a relaxed configuration or partially stretched configuration. The resulting laminate can be made stretchable (or more stretchable in the case of partially stretched strands or film) by subjecting the laminate to an elongation process which elongates the substrate permanently, but elongates the elastic members only temporarily. Such processes are known in the art as "zero strain" stretch laminate formation, and the elongation of such laminates may be accomplished with suitable means such as rollers, engaging teeth, or the like. Examples of zero strain activation processing and formations of resulting stretch laminates are described in U.S. Pat. Nos. 5,167,897 and 5,156,793

An alternate technique for the formation of a stretch laminate is disclosed in U.S. Patent Application Publication Nos. 2003/0088228A1, 2003/0091807A1, and 2004/0222553A1. The technique disclosed in these publications involves forming the elastic member by hot melt application of one or more thermoplastic elastomers onto a substrate, followed by incremental stretching of the substrate that confers the stretch properties of the elastomer to the substrate. Suitable application methods include, for example, direct gravure, offset gravure, and flexographic printing. Each of these methods allows deposition of an amount of elastomer in any shape and direction, thus providing substantial flexibility in the stretch character exhibited by the stretch laminate. Other conventional methods for stretch laminate formation are within the scope of this description.

Additionally, to produce reliable SRSLs, it is important to achieve a relatively uniform strain profile throughout the stretch zone. Materials exhibiting a yield drop may have stability problems during stretching, such as variations in thickness, and thereby generally result in laminates with a high level of property variation. Increasing the stretching temperature, decreasing the strain rate, and/or prestretching the elastic member can make the yield drop less pronounced, thereby improving the chances for achieving a more uniform strain profile. Such results in the fabrication of more reliable stretch laminates.

The elastic member 12 may comprise an elastomeric polymer, optionally at least one modifying resin, and optionally one or more additives. A number of elastomeric polymers, either alone or in combination, can be used to prepare the elastic member 12. Elastomeric polymers include, but are not limited to, homopolymers (e.g., crosslinked poly(isoprene)), block copolymers, random copolymers, alternating copolymers, and graft copolymers. Suitable elastomeric polymers comprise styrenic block copolymers, natural and synthetic rubbers, polyisoprene, neoprene, polyurethanes, silicone rubbers, hydrocarbon elastomers, ionomers, and the like.

In one embodiment, the elastomeric polymer may be a block copolymer. A number of block copolymers may be used including multi-block, tapered block and star block copolymers. Generally, the block copolymers suitable for use in the present invention may exhibit both elastomeric and thermoplastic characteristics. In such block copolymers a hard block (or segment) may have a glass transition temperature (Tg) greater than about 25° C. or is crystalline or semicrystalline with a melting temperature (Tm) above about 25° C. Preferably, the hard block has a Tg greater than about 35° C. or is crystalline or semicrystalline with a Tm above about 35° C. The hard block portion is typically derived from vinyl monomers including vinyl arenes such as styrene and alpha-methyl-styrene or combinations thereof.

Glass transition temperatures referred to herein are determined by tensile dynamic mechanical analysis performed in the linear elastic region of the material at a frequency of 1 Hz using a temperature ramp method. Suitably, film samples with a uniform thickness of about 0.3 mm may be used with a temperature ramp rate of about 1° C./min or slower. The Tan δ peak temperature is taken as the Tg of the particular material or phase.

Crystalline melting temperatures referred to herein are determined by Differential Scanning Calorimetry using a temperature ramp rate of 10° C./min. The melting endothermic peak temperature is taken as the Tm of the particular crystalline region.

The block copolymers may comprise a soft block (or segment). The soft block generally exhibits a sufficiently low glass transition temperature and/or melting temperature so as not to form glassy or crystalline regions at the use temperature of the copolymer. In one embodiment, the use temperature may be between about room temperature (about 22° C.) and about body temperature (about 37° C.). However, other use temperatures are feasible and within the scope of this invention. Such soft blocks are generally physically incompatible with the hard blocks and form separate regions, domains, or phases.

The soft block portion may be a polymer derived from conjugated aliphatic diene monomers. Typically, the monomers used to synthesize the soft block contain fewer than about 6 carbon atoms. Suitable diene monomers include butadiene, isoprene, and the like. Particularly preferred soft block polymers include poly(butadiene) and poly(isoprene). Furthermore, it is envisioned that the soft block may be modified to tailor the Tg of the soft block. For example, a random copolymer of isoprene and styrene or a graft of styrene onto poly(isoprene) may be used. In such cases, lower amounts of the modifying resin may be used.

Suitable block copolymers for use in this invention may comprise at least one hard block (A) and at least one soft block (B). The block copolymers may have multiple blocks. In a preferred embodiment, the block copolymer may be an A-B-A triblock copolymer, an A-B-A-B tetrablock copolymer, or an A-B-A-B-A pentablock copolymer. Also, useful herein are triblock copolymers having endblocks A and A', wherein A and A' may be derived from different vinyl compounds. Also, useful in the present invention are block copolymers having more than one hard block and/or more than one soft block, wherein each hard block may be derived from the same or different monomers and each soft block may be derived from the same or different monomers. It should be noted that where the copolymer contains residual olefinic double bonds, the copolymer may be partially or fully hydrogenated if desired. Saturation may often yield beneficial effects in the elastomeric properties of the copolymer.

The elastic member 12 generally may comprise the elastomeric polymer in amounts from about 20% to about 100%, by weight. In other suitable embodiments, the elastic member 12 generally may comprise the elastomeric polymer in amounts from about 30% to about 65%. Alternatively, the elastic member 12 generally may comprise the elastomeric polymer in amounts from about 45% to about 60%.

In suitable embodiments, elastomeric polymers include styrene-olefin-styrene triblock copolymers such as styrene-butadiene-styrene (S-B-S), styrene-ethylene/butylene-styrene (S-EB-S), styrene-ethylene/propylene-styrene (S-EP- S), styrene-isoprene-styrene (S-I-S), hydrogenated polystyrene-isoprene/butadiene-styrene (S-EEP-S), and mixtures thereof. The block copolymers may be employed alone or in a blend of block copolymers, and may be partially or fully hydrogenated.

In particular embodiments, the elastomeric polymers include styrene-butadiene-styrene (S-B-S) and styrene-isoprene-styrene (S-I-S) block copolymers. Such linear block copolymers of styrene-butadiene-styrene (S-B-S) and styrene-isoprene-styrene (S-I-S) are commercially available under the trade designation Vector from Dexco Polymers L.P., Houston, Tex., and under the trade designation Kraton from Kraton Polymers, Houston, Tex.

The elastic member 12 may comprise one or more modifying resins. Suitable modifying resins should preferably associate or phase mix with the soft blocks of the elastomeric polymer. The elastic member 12 may comprise modifying resins in amounts from about 0% to about 60% by weight. In other embodiments, the elastic member 12 may comprise modifying resins in amounts from about 20% to about 55%. In certain embodiments, the elastic member 12 may comprise modifying resins in amounts from about 40% to about 50%.

Suitable modifying resins useful herein may have glass transition temperatures ranging from about 60° C. to about 180° C., more preferably from about 70° C. to about 150° C., and more preferably from about 90° C. to about 130° C.

Suitable modifying resins may be soft block associating. A solubility parameter is useful in determining whether the modifying resin will phase mix with the soft block of the block copolymer. Generally, modifying resins are selected so that the solubility parameter of the modifying resin is similar to the solubility parameter of the soft block phase. For example in the case where the solubility parameter of the soft block phase is about 8 $(cal/cm^3)^{1/2}$, the solubility parameter of the modifying resin may be from about 7.5 $(cal/cm^3)^{1/2}$ to about 8.5 $(cal/cm^3)^{1/2}$. The solubility parameters of the modifying resins may also approximate the solubility of the hard block. However, so long as the modifying resin phase mixes with the soft block, hard block phase mixing should not be read as limiting. A list of solubility parameters for common polymers or resins, along with methods for determining or approximating the solubility parameters can be found in the *Polymer Handbook*, Third Edition; Wiley Interscience; Section VII pages 519-559.

Modifying resins useful herein include, but are not limited to, unhydrogenated C5 hydrocarbon resins or C9 hydrocarbon resins, partially and fully hydrogenated C5 hydrocarbon resins or C9 hydrocarbon resins; cycloaliphatic resins; terpene resins; polystyrene and styrene oligomers; poly(t-butylstyrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof. Preferably, the resin is selected from the group consisting of the oligomers, polymers and/or copolymers derived from: t-butylstyrene, cyclopentadiene, iso-bornyl methacrylate, methyl methacrylate, isobutyl methacrylate, indene, coumarone, vinylcyclohexane, methylstyrene, and 3,3,5-trimethylcyclohexyl methacrylate. Preferred modifying resins also include alicyclic terpenes, hydrocarbon resins, cycloaliphatic resins, polybeta-pinene, terpene phenolic resins, and combinations thereof. "C5 hydrocarbon resins" and "C9 hydrocarbon resins" are disclosed in U.S. Pat. No. 6,310,154.

The elastic member 12 may comprise a variety of additives. Suitable additives including, for example, stabilizers, antioxidants, and bacteriostats may be employed to prevent thermal, oxidative, and bio-chemical degradation of the elastic member 12. Generally, additives may account for about 0.01% to about 60% of the total weight of the elastic member 12. In other embodiments, the composition comprises from about 0.01% to about 25%. In other suitable embodiments, the composition comprises from about 0.01% to about 10% by weight, of additives.

Various stabilizers and antioxidants are well known in the art and include high molecular weight hindered phenols (i.e., phenolic compounds with sterically bulky radicals in proximity to the hydroxyl group), multifunctional phenols (i.e., phenolic compounds with sulfur and phosphorous containing groups), phosphates such as tris-(p-nonylphenyl)-phosphite, hindered amines, and combinations thereof. Proprietary commercial stabilizers and/or antioxidants are available under a number of trade names including a variety of Wingstay®, Tinuvin® and Irganox® products.

The elastic member 12 may comprise various bacteriostats that are known in the art. Examples of suitable bacteriostats include benzoates, phenols, aldehydes, halogen containing compounds, nitrogen compounds, and metal-containing compounds such as mercurials, zinc compounds and tin compounds. A representative is available under the trade designation Irgasan Pa. from Ciba Specialty Chemical Corporation, Tarrytown, N.Y.

Other optional additives include thermoplastic polymers or thermoplastic polymer compositions which preferentially associate with the hard blocks or segments of the block copolymers. Without intending to be bound by theory, it is believed that these thermoplastic polymers become incorporated into the entangled three-dimensional network structure of the hard phase. This entangled network structure can provide improved tensile, elastic and stress relaxation properties of the elastomeric composition. When the elastomeric polymer comprises a styrenic block copolymer, thermoplastic polymer additives such as polyphenylene oxide and vinylarene polymers derived from monomers including styrene, alpha-methyl styrene, para-methyl styrene, other alkyl styrene derivatives, vinyl toluene, and mixtures thereof, are useful in the present invention because they are generally considered to be chemically compatible with the styrenic hard blocks of the block copolymer.

The elastic member 12 may comprise viscosity modifiers, processing aids, slip agents or anti-block agents. Processing aids include processing oils, which are well known in the art and include synthetic and natural oils, naphthenic oils, paraffinic oils, olefin oligomers and low molecular weight polymers, vegetable oils, animal oils, and derivatives of such including hydrogenated versions. Processing oils also may incorporate combinations of such oils. A particularly preferred processing oil is mineral oil. Viscosity modifiers are also well known in the art. For example, petroleum derived waxes can be used to reduce the viscosity of the slow recovery elastomer in thermal processing. Suitable waxes include low number-average molecular weight (e.g., 600-6000) polyethylene; petroleum waxes such as paraffin wax and microcrystalline wax; atactic polypropylene; synthetic waxes made by polymerizing carbon monoxide and hydrogen such as Fischer-Tropsch wax; and polyolefin waxes.

Various colorants and fillers are known in the art and may be included as additives within the composition that forms the elastic member 12. Colorants can include dyes and pigments such as titanium dioxide. Fillers may include such materials as talc and clay. Other additives may include dyes, UV absorbers, odor control agents, perfumes, fillers, desiccants, and the like.

In certain embodiments of the present invention, it has unexpectedly been found that the elastic member can exhibit a substantially large yield drop. Those trained in the art will appreciate that elastic members which exhibit a yield drop at the characteristic strain rate and temperature of the stretching process may have stability problems during the draw down process, and thereby generally result in SRSLs with unreliable performance for the end user. Additionally, those trained in the art will further appreciate that stability problems observed during the stretching process are not necessarily a result of the elastic member exhibiting a yield drop. Other causes may include, but are not limited to, localized nonuniformities in composition, structure or basis weight, draw resonance, variations in the stretching process, including but not limited to variations in drawing or feed velocity, variations in the temperature of the heating elements, slippage or sticking of the elastic member to rollers or other process contact points, and the wearing-out of guides.

It has been found that elastic members that exhibit one or more of the following as measured by the Process Tensile Test generally lead to a sufficiently uniform strain profile in the stretch zone and thereby a reliable SRSL for the end user: (i) a yield stress drop of about 0.3 MPa or less at the characteristic strain rate and characteristic temperature of the stretching process, (ii) a percent yield stress drop of about 30 percent or less at the characteristic strain rate and characteristic temperature of the stretching process, (iii) a yield stress drop of about 0.15 MPa or less at the initial tensile strain rate equal to the characteristic strain rate of the stretching process and at the characteristic temperature of the stretching process, or (iv) a percent yield stress drop of about 20 percent or less at the initial tensile strain rate equal to the characteristic strain rate of the stretching process and at the characteristic temperature of the stretching process.

Further, it may be desirable for the elastic members to exhibit one or more of the following: (i) a yield stress drop of about 0.25 MPa or less at the characteristic strain rate and characteristic temperature of the stretching process, (ii) a percent yield stress drop of about 25 percent or less at the characteristic strain rate and characteristic temperature of the stretching process, (iii) a yield stress drop of about 0.10 MPa or less at the initial tensile strain rate equal to the characteristic strain rate of the stretching process and at the characteristic temperature of the stretching process, and (iv) a percent yield stress drop of about 10 percent or less at the initial tensile strain rate equal to the characteristic strain rate of the stretching process and at the characteristic temperature of the stretching process.

Additionally, it may be desirable for the elastic members to exhibit one or more of the following: (i) a yield stress drop of about 0.15 MPa or less at the characteristic strain rate and characteristic temperature of the stretching process, (ii) a percent yield stress drop of about 20 percent or less at the characteristic strain rate and characteristic temperature of the stretching process, (iii) a yield stress drop of about 0.05 MPa or less at the initial tensile strain rate equal to the characteristic strain rate of the stretching process and at the characteristic temperature of the stretching process, or (iv) a percent yield stress drop of about 5 percent or less at the initial tensile strain rate equal to the characteristic strain rate of the stretching process and at the characteristic temperature of the stretching process.

There are several methods available to reduce or eliminate the yield drop for a given elastic member. These include, but are not limited to, one or a combination of the following pretreatments: (1) heating the elastic member prior to and sometimes also during the stretching step, where the heating can be accomplished through conductive, convective, radiative, microwave, radiowave, or other heating methods known in the art, (2) prestretching the elastic member with or without added heat, or (3) incrementally stretching the elastic member in a series of steps which stretch and in certain embodiments then relax the elastic member in progressively increasing levels of stretch, with or without added heat. When heating the elastic member, it may be desired to heat it from about 30 to about 100° C., from about 35 to about 70° C., or from about 40 to about 60° C. Those trained in the art will further appreciate that the particular method or combination of methods, as well as the extent to which the elastic member is heated, prestretched, or incrementally stretched, is dependent on the composition and basis weight of the elastic member and on the particular stretch laminate manufacturing process.

In prestretching the elastic member to reduce or eliminate the yield drop of the elastic member, it may be desirable to prestretch the elastic member at least beyond the yield strain measured at the characteristic strain rate and temperature of the stretching process. Further, it may be desirable to pre-stretch the elastic member at least beyond the in-line strain the elastic member will experience in the stretching process. Still further, it may be desirable to prestretch the elastic member to strains at which the engineering stress is larger than the yield stress. If the prestretching strains are larger than the strain at break, then it may be desirable for the prestretching strains to be sufficiently below the average strain at break to ensure minimal breakage during production. And, if the elastic member is prestretched beyond the in-line strain of the manufacturing process, it may be desirable to allow sufficient time for the elastic member to recover to strains at or below the process strain before the SRSL is fabricated. Heating the elastic member can decrease the time needed for the elastic member to recover. Additionally, the process strain may need to be adjusted to achieve the desired in-line product strain. Further, if the characteristic strain rate of the prestretching is too high, it can lead to stability problems similar to those described above for the stretching process. It may be desirable to use as low of a strain rate as practical in order to minimize such stability problems. The prestretching step can usually be carried out at any point between the production of the elastic member and the fabrication of the SRSL.

In using incremental stretching of the elastic member to reduce or eliminate the yield drop of the elastic member, it may be desirable to perform the stretching operation in several stages. For example, by passing the elastic member through a series of rolls where the first pair of rolls stretch the elastic member, the second pair allow the elastic member to relax, the third pair stretch the elastic member to a greater extent than the first pair, the fourth pair allow the elastic member to relax, and so on through a series of stretch-relaxation roll combinations. The use of multiple roll pairs with progressively greater degrees of stretching imposes a lower strain rate on the elastic member than would be the case for a single pair of stretching rolls having a level of stretching comparable to the final pair of multiple rolls. In addition, the temporary relaxation of the elastic member as it passes between successive stretch roll pairs allows some degree of stress redistribution to occur in the elastic member prior to the elastic member being stretched to a greater degree by the succeeding roll pair. Minimizing the strain rate and allowing a degree of stress redistribution reduces the chances for stability problems to arise during the stretching process.

Further, in using incremental stretching, it may be desirable that the first pair of stretch rolls stretch the elastic member at least beyond the yield strain measured at the characteristic strain rate and temperature of the stretching process.

Additionally, if the level of stretching in the final pair of stretch rolls is larger than the in-line strain of the manufacturing process, it may be desirable to allow the elastic member to recover in the final pair of relaxation rolls to strains at or below the process strain before the SRSL is fabricated. Heating the elastic member can decrease the time needed for the elastic member to recover and thereby allow for a higher line speed of manufacture. Additionally, the process strain may need to be adjusted to achieve the desired in-line product strain.

Still further, for any pair of stretch rolls imparting a level of stretch to the elastic member below the strain corresponding to the post yield minimum stress measured at the characteristic strain rate and temperature of the stretching process, if the characteristic strain rate is too high it can lead to stability problems similar to those described above for the stretching process. It may be desirable to use as low of a strain rate as practical in order to minimize such stability problems. The incremental stretching process can usually be carried out at any point between the production of the elastic member and the fabrication of the SRSL.

Further, in using incremental stretching for certain embodiments of the present invention, it may be desirable to minimize or prevent the relaxation of the elastic member between one or more of the stretching steps. For example, it may be desirable to only have incrementally increasing levels of stretch between successive pairs of rolls. This approach may be desirable to minimize the strain rate and reduce the chances for stability problems to arise during the stretching process, while possibly leading to a higher tensile modulus of elasticity than when the relaxation steps are included. A higher modulus can lead, for example, to easier web handling of the elastic member during the production of a SRSL.

For certain embodiments of the present invention, it may be desirable to wait at least about 12 hours (particularly including 24 hours) after the production, before initiating the pretreatment process. While not wishing to be bound by theory, it is believed that for certain embodiments, sufficient time may be given for the morphology of the elastic member to fully develop. Various analytical methods can be used to determine how long after the production of a specific elastic member it is preferred to wait before initiating the pretreatment process. For example, one may monitor the post elongation recovery of the elastic member using the method disclosed in U.S. patent application Ser. No. 11/114,508.

Suitable substrates 14 for use include nonwoven webs, woven webs, knitted fabrics, films, film laminates, apertured films, nonwoven laminates, sponges, foams, scrims, and any combinations thereof. Suitable substrates may comprise natural materials, synthetic materials, or any combination thereof. For use in absorbent articles and particularly in diapers and like products, the substrate 14 is generally compliant, soft-feeling, and non-irritating to a wearer's skin. In certain embodiments, substrates 14 may include nonwoven webs such as spunbond webs, meltblown webs, carded webs, and combinations thereof (e.g., spunbond-meltblown composites and variants).

The dimensions of the substrate 14 are generally limited only by the requisite end-use of the SRSL 10.

The SRSL 10 of the present invention exhibits unique elastic and recovery characteristics. The SRSL 10 exhibits a normalized unload force of greater than about 0.16 N/(g/m) at 37° C. as measured by the Two Cycle Hysteresis Test. Normalized unload forces of less than about 0.12 N/(g/m) at 37° C. are believed to be insufficient for use as an elastomer within absorbent articles. Laminates having normalized unload forces less than 0.12 N/(g/m) at 37° C. are unable to keep an absorbent article in snug, close contact to the wearer's skin. In certain embodiments, the SRSL 10 exhibits a normalized unload force of greater than about 0.24 N/(g/m) at 37° C.

Conventional stretch laminates (i.e., such as those commonly found in absorbent articles including diapers) exhibit minimal post elongation strain at 22° C. after 15 seconds of recovery. Qualitatively, conventional stretch laminates exhibit "snap back" (i.e., contracts relatively quickly after being released from a stretched state). In contrast, the SRSL 10 of the current invention exhibit a percent of initial strain of about 10% or greater after 15 seconds of recovery at 22° C., as measured by the Post Elongation Recovery Test. In other embodiments, the SRSL 10 exhibits a percent of initial strain of about 20% or greater after 15 seconds of recovery at 22° C. In other suitable embodiments, the SRSL 10 exhibits a percent of initial strain of about 30% or greater after 15 seconds of recovery at 22° C. In other suitable embodiments, the SRSL, 10 exhibits a percent of initial strain of about 40% or greater after 15 seconds of recovery at 22° C.

Furthermore, the SRSL 10 of the present invention may exhibit a specified percent of initial strain at 22° C. after 30 seconds, 60 seconds, or three minutes of recovery. In certain embodiments, the SRSL 10 may exhibit a percent of initial strain at 22° C. after 30 seconds of recovery of about 10% or greater. Alternatively, the SRSL 10 may exhibit a percent of initial strain at 22° C. after 30 seconds of recovery about 15% or greater. In other embodiments, the SRSL 10 may exhibit a percent of initial strain at 22° C. after 60 seconds of recovery of about 10% or greater.

The SRSL 10 may exhibit temperature responsiveness. In certain embodiments, the SRSL 10 exhibits a percent of initial strain at 32° C. after a specified amount of recovery time that is less than the percent of initial strain exhibited at 22° C. after the same recovery time. In one embodiment, a temperature responsive SRSL 10 may exhibit a reduction in a percent of initial strain after 15 seconds at 32° C. as compared to the percent of initial strain exhibited after 15 seconds at 22° C. (i.e., [percent of initial strain after 15 seconds of recovery at 22° C.]−[percent of initial strain after 15 seconds of recovery at 32° C.]). In some embodiments, the difference is equal to or greater than 5%. In other embodiments, the SRSL 10 may exhibit a difference in the percent of initial strain after 15 seconds at 22° C. compared to after 15 seconds at 32° C. equal to or greater than 10%, 20%, 30%, or, alternatively, 40%. It is believed that a SRSL 10 exhibiting temperature responsiveness may further facilitate diaper application. When the diaper is applied at about room temperature (i.e., approximately 22° C.), the SRSL 10 may exhibit a relatively high percent of initial strain for a prescribed period of time, which allows the caregiver or wearer to apply the diaper. Upon application of the diaper, the temperature of the SRSL 10 will rise as a result of being in close proximity to the wearer's skin. As the temperature of the SRSL 10 increases and nears skin temperature (i.e., approximately 32° C.), the percent of initial strain is reduced. Temperature responsiveness allows for application of the diaper without "snap-back" while providing for increased recovery after application.

The SRSL 10 may be utilized in a variety of consumer and commercial products. However, the SRSL 10 has particular benefit within absorbent articles, particularly disposable absorbent articles such as diapers and the like. The SRSL 10 may be used in a variety of regions or in a variety of article elements to provide elastic character to the absorbent article. It may be desirable to incorporate the SRSL 10 of the present invention into the absorbent articles disclosed in U.S. Pub. Nos. 2005-0273071, 2005-0171499, 2007-0191806, 2004-0162538, and 2005-0095942.

Another embodiment of the present invention is directed toward a method of applying any of the absorbent articles as disclosed above. The absorbent article may be provided to a caregiver for application onto a wearer. The absorbent article may be in a compacted state such that a stretch laminate comprising a SRSL is in a relaxed, substantially untensioned state. The caregiver may stretch the absorbent article thereby expanding and tensioning the stretch laminate. The article is generally stretched in preparation for application. The absorbent article can maintain a functionally elongated state for an effective period of time. In one embodiment, the article may maintain an elongated state for a sufficient amount of time necessary for the caregiver to apply the article to the wearer. Upon release of the diaper after stretching, the diaper often contracts and/or folds before it can be successfully applied to a wearer. In one embodiment, SRSL exhibits a percent of initial strain after 15 seconds of recovery at 22° C. of greater than or equal to 10%. After application, the article may continue to contract so as to provide a snug, ideal fit. This method may be repeated upon soiling of the article during wear.

In another embodiment, a plurality of absorbent articles as disclosed above may be packaged in a kit. Generally, the kit allows for a quantity of absorbent articles to be delivered to and purchased by a consumer while economizing space and simplifying transport and storage. The kit may require activation so that the article becomes accessible (e.g., opening of a lid, removal of a panel, etc.). In one embodiment, the kit is defined by numerous absorbent articles bound together as an entity and covered by a thermoplastic film overwrap as disclosed in U.S. Pat. No. 5,934,470. The thermoplastic film cover may contain an opening means to allow removal of a portion of the thermoplastic film cover and access to the articles. A typical opening means may include a substantially continuous line of weakness, preferably perforations within the thermoplastic film cover. An exemplary opening means is presented in U.S. Pat. No. 5,036,978.

While one kit embodiment is described above, other variations to the kit are clearly envisioned. The overwrap may comprise a variety of materials including, but not limited to, thermoplastic films, nonwovens, wovens, foils, fabrics, papers, cardboard, elastics, cords, straps, and combinations thereof. The overwrap may completely or partially bind and/ or cover the plurality of absorbent articles. Other particularly preferred packages and methods for packaging are disclosed in U.S. Pat. Nos. 5,050,742 and 5,054,619. Furthermore, a kit may contain multiple overwraps. For example, a plurality of absorbent articles of the present inventions may be packaged with a thermoplastic film overwrap and then a plurality of film wrapped pull-on garments being overwrapped in a cardboard box or a second thermoplastic film overwrap. Furthermore, the kit may not contain a dedicated opening means. For example, a thermoplastic film overwrap without perforation may simply be opened by tearing the film.

Test Methods
Post Elongation Recovery

This method is used to determine the post elongation strain of a stretch laminate as a function of temperature and time. The measurement is done at 22° C. (72° F.) or at 32° C. (90° F.). The measurement at 22° C. (72° F.) is designed to simulate the recovery of the stretch laminate at room temperature, while the measurement at 32° C. (90° F.) is designed to measure the recovery of the stretch laminate near skin temperature. A two-step analysis, Stretch and Recovery, is performed on the samples. The method employs a Dynamic Mechanical Analyzer. A TA Instruments DMA 2980 (hereinafter "DMA 2980"), available from TA Instruments, Inc., of New Castle, Del.; equipped with a film clamp, Thermal Advantage/Thermal Solutions software for data acquisition, and Universal Analysis 2000 software for data analysis was used herein. Many other types of DMA devices exist, and the use of dynamic mechanical analysis is well known to those skilled in the art of polymer and copolymer characterization.

Methods of operation, calibration and guidelines for using the DMA 2980 are found in TA Instruments DMA 2980 Operator's Manual issued March 2002, Thermal Advantage User's Reference Guide issued July 2000 and Universal Analysis 2000 guide issued February 2003. To those skilled in the use of the DMA 2980, the following operational run conditions should be sufficient to replicate the stretch and recovery of the samples.

The DMA 2980 was configured to operate in the Controlled Force Mode with the film clamp. The film clamp is mounted onto the DMA 2980 and calibrated according to the User's Reference Guide. The stretch laminate to be tested is cut into samples of substantially uniform dimension. For the DMA 2980, suitable sample dimensions are approximately 20 mm×6.4 mm×1.0 mm (length×width×thickness). The sample thickness is dependent on the materials and structure of the stretch laminate and on the confining pressure used to measure the thickness. TA Instruments recommends the sample thickness, when securely mounted within the film clamps, to be less than or equal to about 2.0 mm. The lower film clamp of the DMA 2980 is adjusted and locked in a position which provides approximately 10 mm between the clamping surfaces. The sample is mounted in the film clamps and the lower clamp is allowed to float to determine the gauge length between the film clamps. It should be understood that the sample referenced in this method is one where the SRSL must run from the upper clamp to the lower clamp. The sample ID and dimensions are recorded. The film clamp is locked in position and the furnace is closed.

Stretch Method—For the sample dimensions specified above, the DMA 2980 is configured as follows: Preload force applied to sample in clamp (0.01N); auto zero displacement (on) at the start of the test; furnace (close), clamp position (lock), and temperature held at $T_i$ (22° C. or 32° C.) at the end of the stretch method. Data acquisition rate is set at 0.5 Hz (1 point per 2 seconds). The stretch method is loaded onto the DMA 2980. The method segments are (1) Initial Temperature $T_i$ (22° C. or 32° C.), (2) Equilibrate at $T_i$ (3) Data Storage ON, and (4) Ramp Force 5.0 N/min to 18.0 N.

Upon initiation of the test, the temperature ramps to the specified $T_i$ (22° C. or 32° C.) [method segment 1], and the temperature is maintained at this $T_i$ [method segment 2]. After a minimum of 15 minutes at $T_i$, the operator initiates the sample stretching and concurrent data collection [method segments 3 and 4]. The sample is stretched with an applied ramp force of 0.8 N/min per millimeter of initial sample width (e.g., for the sample dimensions specified above, the applied ramp force is 5 N/minute) to approximately 30 mm in length. The gradual increase in force more closely simulates application of the article and prevents sample breakage. The sample is locked in place at the stretched length of approximately 30 mm and maintained at $T_i$. The force required to stretch the laminate to a length of approximately 30 mm and the percent strain of the laminate at this length are recorded manually from the digital readout on the instrument. The percent strain is calculated by subtracting the gauge length from the stretched length, then dividing the result by the gauge length and multiplying by 100. The initial percent strain is described by the equation below:

$$\text{Initial Percent Strain} = \% \text{Strain}_i = 100 \times ((L_s - L_g)/L_g)$$

where $L_g$ is the length of the gathered stretch laminate in a relaxed state and $L_s$ is the length of the stretched laminate between the film clamps at the end of the stretch step of the analysis (~30 mm). % Strain$_i$ is the percent strain of the stretch laminate at the start of the recovery method (i.e. after the stretch part of the method is complete). A sample stretched from a gauge length of 10 mm to a length of 30 mm results in a percent strain of 200%.

Stretch laminates may be unable to exhibit extensibility of 200% strain without incurring irreversible deformation, delamination, tearing, or a significant percent set (i.e., set of greater than about 10%). This is particularly true for stretch laminates obtained from commercially available products such as the side panels, leg cuffs and waistbands of diapers. For example, a stretch laminate (~6.4 mm wide) may be easily stretched to 100% strain or 150% strain when relatively low forces (<4N) are applied. However, if the applied force continues to increase to achieve 200% strain, the percent strain of the stretch laminate plateaus and further extension may be difficult and/or may result in irreversible deformation, delamination, tearing, or significant percent set (i.e., set of greater than 5%) of the stretch laminate. For purposes of this test, the maximum percent strain (e.g., 200%, 150%, or 100%) is to be chosen such that the strain does not result in irreversible deformation, delamination, tearing, or a significant percent set (i.e., set of greater than 5%) of the stretch laminate. If the stretch laminate has an extensibility of less than 200% strain (±5%), a new specimen of the sample is stretched from a gauge length of 12 mm to an extended length of 30 mm which results in a percent strain of 150%. If the stretch laminate has an extensibility of less than 150% strain (±5%), a new specimen of the sample is stretched from a gauge length of 15 mm to an extended length of 30 mm which results in a percent strain of 100% strain. Testing of stretch laminates with maximum extensibility of <100% is also within the scope of this method. For laminates with maximum extensibility of 50% to 94% the post elongation strain is reported as the percent strain rather the percent of initial % strain at the different times of recovery (15 seconds, 30 seconds, 60 seconds and 3 minutes).

For samples of different dimensions, the applied force to stretch the sample is adjusted to achieve an applied ramp force of 0.8 N/min per millimeter of initial sample width. For example, a force ramp of 2.5 N/min is applied to a sample with an initial width of 3.2 mm. For samples of different lengths, the total displacement during the elongation is adjusted to achieve an initial percent strain of 200% (or less if the sample has limited extensibility, i.e. 150% or 100% strain).

Recovery Method—The Recovery Method is loaded onto the instrument and initiated approximately 15 seconds after reaching the desired initial percent strain (i.e. 200%, 150%, or 100%) in the Stretch Method. The four segments of the recovery method are (1) Data Storage ON, (2) Force 0.01N, (3) Ramp to $T_i$, and (4) Isotherm for 3.0 minutes. The following DMA 2980 parameter setting is changed from the Stretch Method: auto zero displacement is changed to (OFF). The Recovery Method measures the length of the sample over a 3 minute time period at the specified temperature ($T_i$=either 22° C. or 32° C.). The sample length, percent strain, and test temperature are recorded as a function of recovery time. The post elongation strain is reported as the percent of the initial percent strain after different times of recovery (15 seconds, 30 seconds, 60 seconds, and 3 minutes).

For samples of different dimensions, the force applied to the sample during recovery (segment 2 above) is adjusted to achieve an applied force of 0.0016 N per millimeter of initial sample width (0.01N for 6.4 mm wide sample). For example, a force of 0.005 N is applied to a sample 3.2 mm wide.

Two Cycle Hysteresis Test

This method is used to determine properties that may correlate with the forces experienced by the consumer during application of the product containing the SRSL and how the product fits and performs once it is applied.

The Two Cycle Hysteresis Test method is performed at room temperature (21° C./70° F.) and also at body temperature (37° C./99° F.). The stretch laminate to be tested is cut into a sample of substantially rectilinear dimensions. Sample dimensions are selected to achieve the required strain with forces appropriate for the instrument. Suitable instruments for this test include tensile testers commercially available from MTS Systems Corp., Eden Prairie, Minn. (e.g. Alliance RT/1 or Sintech 1/S) or from Instron Engineering Corp., Canton, Mass. For either the Alliance RT/1 or Sintech 1/S instruments listed above, suitable sample dimensions are approximately 25 mm wide by approximately 100 mm long. The sample thickness is dependent on the materials and structure of the stretch laminate and on the confining pressure used to measure the thickness. The thicknesses of samples are typically 0.5 mm to 5 mm thick measured with 0.2 psi confining pressure. However, testing of stretch laminates with different thicknesses (e.g., <0.5 mm or >5 mm) is within the scope of this method.

The following procedure illustrates the measurement when using the above sample dimensions and either an Alliance RT/1 or Sintech 1/S. The instrument is interfaced with a computer. TestWorks 4™ software controls the testing parameters, performs data acquisition and calculation, and provides graphs and data reports.

The widths of the grips used for the test are greater than or equal to the width of the sample. Typically 1" (2.54 cm) wide grips are used. The grips are air actuated grips designed to concentrate the entire gripping force along a single line perpendicular to the direction of testing stress having one flat surface and an opposing face from which protrudes a half round (radius=6 mm) to minimize slippage of the sample. In the case of the measurement at 37° C., the upper grip is a lightweight grip with serrated faces.

The load cell is selected so that the forces measured will be between 10% and 90% of the capacity of the load cell or the load range used. Typically a 25 N load cell is used. The fixtures and grips are installed. The instrument is calibrated according to the manufacturer's instructions. The distance between the lines of gripping force (gauge length) is 2.50" (63.5 mm), which is measured with a steel ruler held beside the grips. The load reading on the instrument is zeroed to account for the mass of the fixture and grips. The specimen is equilibrated a minimum of 1 hour at 21° C. before testing. The specimen is mounted into the grips in a manner such that there is no slack and the load measured is between 0.00 N and 0.02 N. It should be understood that the specimen referenced in this method is one where the SRSL must extend along the entirety of the gauge length. The instrument is located in a temperature-controlled room for measurements performed at 21° C. A suitable environmental chamber is used to maintain the testing temperature for measurements performed at 37° C.; the sample is mounted in the grips and equilibrated for 5 minutes at 37° C. before starting the test. For purposes of this test, the specified initial percent strain Strain$_i$ (e.g., 150%, 100% or 70%) is to be chosen such that the strain does not result in irreversible deformation, delamination, tearing, or a significant percent set (i.e., set of greater than about 10%) of the stretch laminate. Testing of stretch laminates with initial extensibility of <70% is also within the scope of this method, however the unload force is measured at a strain equal to 75% of the specified initial percent strain. For example, if the specified initial percent strain is 60%, the unload force is measured at 45% strain.

The Two Cycle Hysteresis Test method involves the following steps:
(1) Strain the sample to the specified initial percent strain (e.g., Strain$_i$=150%) at a constant crosshead speed of 20"/min. (50.8 cm/min) with no hold.
(2) Reduce the strain to 0% strain (i.e., return grips to the original gauge length) at a constant crosshead speed of 3"/min. (7.62 cm/min) with no hold.
(3) Strain the sample to Strains at a constant crosshead speed of 20"/min. (50.8 cm/min) with no hold.
(4) Reduce the strain to 60% strain at a constant crosshead speed of 3"/min. (7.62 cm/min). If Strain$_i$<70%, reduce the strain to 75% of Strain$_i$.
(5) Hold the sample at 60% strain for 5 minutes. If Strain$_i$<70%, hold the sample at 75% of Strain$_i$.
(6) Go to 0% strain at a constant crosshead speed 3"/min. (7.62 cm/min)

The reported unload force is the measured unload force of the stretch laminate (SL) at 60% strain (or at 75% of Strain$_i$, in cases where Strain$_i$<70%), after the 5 minute hold in step 5, normalized to Newton per 1 meter width of SL*basis weight of elastomer+adhesive (E+A) in the SL, N/(m·gsm)=N/(g/m), as shown in the equation below. The basis weight of the elastic and adhesive in the SL is calculated by dividing the grams of elastomer+adhesive in the SL by the area of the SL fully extended. The area of the fully extended stretch laminate ($A_{FSEL}$) is defined as the area of the substrate of the stretch laminate in the absence of elastic and adhesive.

The normalized unload force in N/(m·gsm) =

$$N/(g/m) = \frac{\text{measured unload force (N)}}{[\text{width of } SL \text{ in meters} * ((\text{grams of } E+A) \div A_{FSEL} \text{ in m}^2)]}.$$

For different sample dimensions, the crosshead speed is adjusted to maintain the appropriate strain rate for each portion of the test. For example, a crosshead speed of 10"/min (25.4 cm/min) would be used in Steps 1 and 3 for a sample gauge length of 1.25" (31.7 mm).

Process Tensile Test

This method is used to determine the engineering stress versus strain curve of the elastic member. The measurement is carried out at a cross-head speed and temperature that approximates the characteristic strain rate and characteristic temperature of the stretching process of interest.

The first step is to determine the corresponding cross-head speed, which is dependent on the particular stretching process. While there are a variety of stretching processes used in the industry, the most common approach is to route the elastic member through a series of temperature controlled rollers, each with a faster surface speed than the one before, such as described by A. Ziabicki in *Fundamentals of Fibre Formation*, John Wiley & Sons, New York (1976), Chapter 6. For a one-stage (two roll) stretching process, the average process strain rate $\langle \dot{\epsilon} \rangle_{process}$ can be estimated from the differential roll speed and the span length over which the draw down occurs, namely $$\langle \dot{\epsilon} \rangle_{process} = \frac{V_{pull} - V_{feed}}{L_{span}} \quad [1]$$

where $V_{pull}$ is the pull velocity acting on the elastic member, $V_{feed}$ the feed velocity of the elastic member into the draw down process, and $L_{span}$ the span length over which the elastic member is drawn down. Those trained in the art will recognize that the span length may be shorter than the path length distance between the feed and pull rolls. The relationship between the roll speeds and the engineering process strain $\gamma_{process}$ is given by $$\frac{V_{pull}}{V_{feed}} - 1 = \frac{\gamma_{process}}{100} \quad [2]$$

where $\gamma_{process}$ is in units of percent.

Those trained in the art will also recognize that in multi-stage stretching processes, for example, stretching processes with 3 or more draw rolls with or without drawpins, there can be different average strain rates between each pair of rolls but that the average strain rate and process strain for each draw region can be represented by equations equivalent to Eq. [1] and Eq. [2]. Additionally, those trained in art will also recognize that in alternative stretching processes such as, but not limited to, uniform stretching methods like tentering such as described by J. H. Briston in *Plastic Films*, 2$^{nd}$ Edition, Longman Inc., New York (1983), pages 83-85, or incremental stretching methods like ring rolling such as disclosed in U.S. Pat. Nos. 4,116,842 and 5,296,184 where alternating parallel regions that are stretched coexist with regions that remain virtually unstretched, the average strain rate and process strain for each draw region can be represented by equations equivalent to Eq. [1] and Eq. [2]. In each of these cases, it is important to recognize that both the average strain rate and process strain of interest will be where the elastic member passes through the yield point.

In a typical tensile test with a constant cross-head speed $C_H$, the average tensile strain rate $\langle \dot{\epsilon} \rangle_{tensile}$ to draw down the elastic member from it's initial (gauge) length $L_o$ to any given stretch length L can be estimated in a manner similar to Eq. [1], namely:

$$\langle \dot{\epsilon} \rangle_{tensile} = \frac{C_H}{L - L_o} \quad [3]$$

For the case of L approaching $L_o$ (L→$L_o$), i.e., the initial tensile strain rate, it is more convenient to use the following:

$$\langle \dot{\epsilon} \rangle_{tensile \atop L \to L_o} = \frac{C_H}{L_o} \quad [4]$$

The relationship between the stretch length and the engineering tensile strain $\gamma_{tensile}$ is given by $$\frac{L}{L_o} - 1 = \frac{\gamma_{tensile}}{100} \quad [5]$$

where $\gamma_{tensile}$ is in units of percent.

For the tensile test to approximate the on-line stretching process, two cases are identified:

Case 1: The average strain rate in the tensile test (up to a tensile strain equivalent to the process strain) is equal to the average process strain rate. In this case $\gamma_{tensile} = \gamma_{process}$, and combining this equality with Eqs. [1]-[3] and [5] leads to $$C_H = V_{feed} \frac{L_o}{L_{span}} \left(\frac{\gamma_{process}}{100}\right)^2 \quad [6]$$

or equivalently $$C_H = V_{pull} \frac{L_o}{L_{span}} \frac{\left(\frac{\gamma_{process}}{100}\right)^2}{\left(1 + \frac{\gamma_{process}}{100}\right)} \quad [7]$$

Case 2: The initial strain rate in the tensile test is equal to the average process strain rate. Combining Eqs. [1], [2], and [4] results in $$C_H = V_{feed} \frac{L_o}{L_{span}} \left(\frac{\gamma_{process}}{100}\right) \quad [8]$$

or equivalently $$C_H = V_{feed} \frac{L_o}{L_{span}} \frac{\left(\frac{\gamma_{process}}{100}\right)}{\left(1 + \frac{\gamma_{process}}{100}\right)} \quad [9]$$

With the cross-head speed defined, the tensile test is performed at the characteristic temperature of the stretch process of interest. The material to be tested is cut into a substantially rectilinear shape. Sample dimensions are selected to achieve the required strain with forces appropriate for the instrument. Suitable instruments for this test include tensile testers commercially available from MTS Systems Corp., Eden Prairie, Minn. (e.g. Alliance RT/1 or Sintech 1/S) or from Instron Engineering Corp., Canton, Mass. For either the Alliance RT/1 or Sintech 1/S instruments listed above, suitable sample dimensions are approximately 0.15 mm thick, approximately 20 mm wide by approximately 100 mm long.

The following procedure illustrates the measurement when using the above sample dimensions and either an Alliance RT/1 or Sintech 1/S. The instrument is interfaced with a computer. TestWorks 4™ software controls the testing parameters, performs data acquisition and calculation, and provides graphs and data reports.

The grips used for the test are wider than the elastic member. Typically 1.00 inch (2.54 cm) wide grips are used. The grips are air actuated grips designed to concentrate the entire gripping force along a single line perpendicular to the direction of testing stress having one flat surface and an opposing face from which protrudes a half round (radius=6 mm) to minimize slippage of the sample. The load cell is selected so that the forces measured will be between 10% and 90% of the capacity of the load cell or the load range used. Typically a 100 N load cell is used. The fixtures and grips are installed. The instrument is calibrated according to the manufacturer's instructions. The ramp step acceleration, a control parameter for motion, is set to 1,000 to ensure the specified crosshead speed is achieved before the yield point. The distance between the lines of gripping force (gauge length) is 1.00 inch (25.4 mm), which is measured with a steel ruler held beside the grips. The load reading on the instrument is zeroed to account for the mass of the fixture and grips. The mass and thickness of the specimen are measured before testing. The specimen is mounted into the grips in a manner such that there is no slack and the load measured is between 0.00N and 0.05N. For measurements done at elevated temperatures (for example, 40° C.), the sample is equilibrated at the testing temperature for approximately 5 minutes before starting the test. A suitable environmental chamber is used to maintain the temperature at 40° C. for measurements performed at this temperature. The instrument is located in a temperature-controlled room for measurements performed at 22° C. A minimum of five samples is used to determine the average test values.

Figure 3:
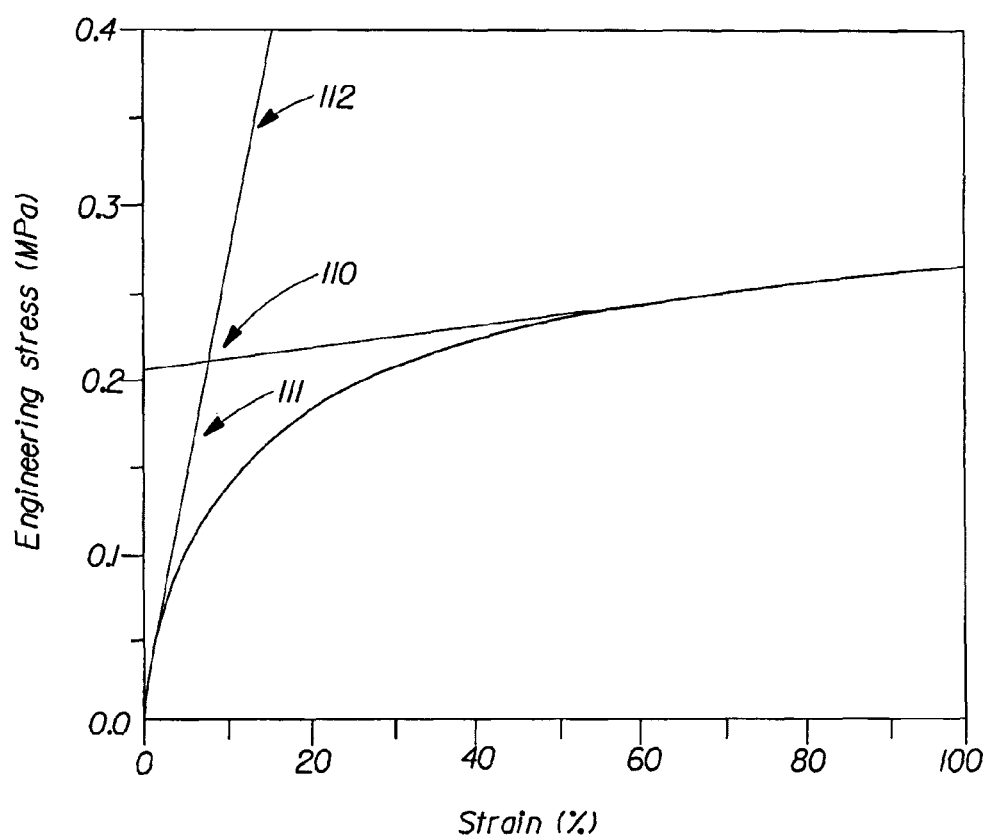
FIG. 3 is an example engineering stress-strain curve for a material that does not exhibit a yield drop.

For materials that exhibit a yield drop, such as shown in FIG. 2, the yield point 100 identifies the yield stress 101, the yield strain 102, the post yield minimum stress 103, and the yield stress drop 104. For materials that do no exhibit a yield drop, such as shown in FIG. 3, the yield point 110 is estimated using the method outlined by I. M. Ward in *Mechanical Properties of Solid Polymers*, Wiley-Interscience, New York (1971), page 278. Namely, the yield point occurs where the two tangents to the initial 111 and secondary 112 parts of the stress-strain curve intersect. Additionally, for materials that do not exhibit a yield drop, the yield stress drop is zero.

Two Cycle Fit Test

This method is used to determine the SRSL properties that may correlate with the forces experienced by the consumer during application of the product containing the SRSL and may also correlate to how the product fits and performs in use.

The Two Cycle Fit Test method is performed at room temperature (22° C./72° F.) and also at body temperature (37° C./99° F.). The SRSL to be tested is cut into a sample of substantially rectilinear dimensions. The sample dimensions are selected to achieve the required strain with forces appropriate for the instrument. Additionally, sample dimensions are selected based on the specifications of the product and the lamination process. Suitable instruments for this test include tensile testers commercially available from MTS Systems Corp., Eden Prairie, Minn. (e.g. Alliance RT/1 or Sintech 1/S) or from Instron Engineering Corp., Canton, Mass. For either the Alliance RT/1 or Sintech 1/S instruments listed above, suitable sample dimensions are approximately 210 mm wide by approximately 451 mm long. The sample thickness is dependent on the materials and structure of the SRSL and on the confining pressure used to measure the thickness. The thicknesses of samples are typically 0.5 mm to 5 mm thick measured with 0.2 psi confining pressure. However, testing of SRSL with different thicknesses (e.g., <0.5 mm or >5 mm) are within the scope of this method. Additionally, a SRSL with a different width or length are within the scope of this method.

The following procedure illustrates the measurement when using the above sample dimensions and either an Alliance RT/1 or Sintech 1/S. The instrument is interfaced with a computer. TestWorks 4™ software controls the testing parameters, performs data acquisition and calculation, and provides graphs and data reports.

Figure 4:
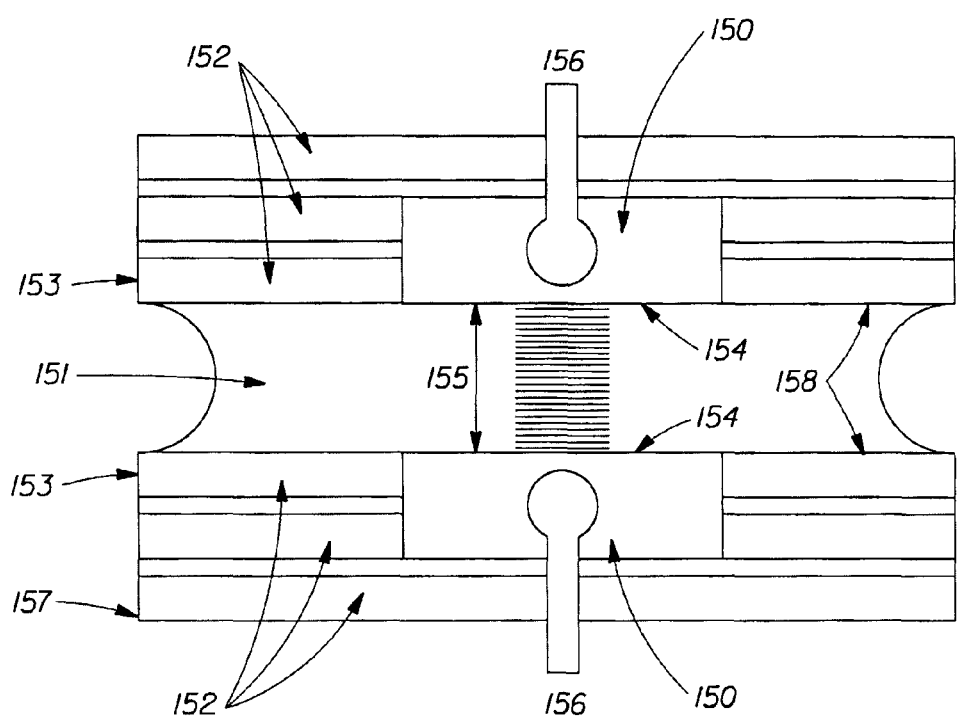
FIG. 4 is an illustration of the Two Cycle Fit Test's equipment configuration and test sample loading.

Typically, as shown in FIG. 4, a pair of flat SBR faced grips 150 with dimensions of approximately 2" (5.08 cm) wide by 1" (2.54 cm) tall is used in combination with a sample holder 153. The width of the sample holders 153 used for the test is greater than or equal to the width of the SRSL sample 151. The grips 156 are air actuated and designed to concentrate the entire gripping force between two flat SBR faced surfaces to minimize slippage of the sample holder 153. The sample holder 153 is made of two rectilinear pieces of LEXAN with dimensions of approximately 50 mm tall by approximately 210 mm wide by approximately 1.5 mm thick. Each piece of the sample holder 153 has three approximately 10 mm tall× 210 mm wide strips of hook material 152 (for example, such as used in diaper fasteners) attached to one face at the top, middle and bottom. The strips of hook material 152 are used to secure the SRSL sample 151 in the sample holder 153 and to minimize slippage of the SRSL sample 151 in the sample holder 153.

Preparation of SRSL Test Samples from a Continuous Lamination Process is Done Using the following procedure. Samples are taken from throughout the laminate production. In the present example, a 1 minute production of laminates at 100 units per minute produces a continuous SRSL with a longitudinal length equivalent to 100 SRSLs, wherein "unit" is the product length, which is 451 mm. Stretch the continuous SRSL sample from the SRSL production until the SRSL is fully extended (no visual gathering and not over-extended). Mark the nonwoven of the SRSL across the lateral direction, perpendicular to the longitudinal direction at lengths of 451 mm apart, where the longitudinal direction is the machine direction of the lamination process. Additionally, mark the nonwoven 50 mm on each side of the 451 mm mark. Cut the 451 mm long SRSL units and sample 2 laminates every tenth unit to provide 2 sets of n=10 for testing at room temperature (22° C.) & body temperature (37° C.). Each SRSL sample is approximately 451 mm long, when fully extended, and is marked 50 mm from both ends, so the distance between the "50 mm" marked lines is approximately 351 mm. After cutting, the SRSL samples are conditioned at 22° C. for a minimum of 24 hours before testing.

Also, referring to FIG. 4, the SRSL sample 151 is placed in the sample holders 153, keeping the SRSL sample 151 flat (no gathers in the nonwoven between the sample holders 153) and with the "50 mm" marked lines from each end of the SRSL sample 151 in line with the inner edges 154 of the sample holders 153 and with the ends of SRSL sample 151 in line with the outer edges 157 of the sample holders 153 at all four corners. The sample holders 153 are placed in the grip faces 150 so that the inner edges 158 of the sample holders 153 are in line with the inner edges 154 of the grip faces 150. The inner edges 154 of the top and bottom grip faces 150 are separated to a distance 155 of approximately 61 mm. When the sample holder 153 containing the SRSL sample 151 is placed between the grip faces 150, there is slack in the SRSL sample 151. For example, the gathered SRSL sample 151 within the 61 mm gauge length has a 351 mm length when fully extended. During the Two Cycle Fit Test, the SRSL sample 151 is stretched to an extended gauge length of 305 mm, which corresponds to approximately 87% fully extended SRSL sample 151 between the inner edges 154 of the grip faces 150.

The load cell is selected so that the forces measured will be between 10% and 90% of the capacity of the load cell or the load range used. Typically a 25 N load cell is used. The fixtures, grips 156, grip faces 150, and sample holders 153 are installed. The instrument is calibrated according to the manufacturer's instructions. The distance 155 between the lines of gripping force (gauge length) is 2.4" (61 mm) which is measured with a steel ruler held beside the grip faces 150.

The SRSL sample is equilibrated a minimum of 24 hours at 22° C. before testing. The sample holder 153 containing the SRSL sample 151 is mounted between the grip faces 150 in a manner such that there is slack as described above. The instrument is located in a temperature-controlled room for measurements performed at 22° C. A suitable environmental chamber is used to maintain the testing temperature for measurements performed at 37° C.; the SRSL sample 151 is mounted as described above and equilibrated for approximately 5 minutes at 37° C. before starting the test.

The Two Cycle Fit Test method involves the following steps, with a constant crosshead speed of 20"/minute (50.8 cm/min):
(1) The load reading on the instrument is zeroed (0.00 N) before starting the test.
(2) Strain the SRSL sample 151 to the specified laminate fit strain (400%) with no hold; i.e., 400% laminate fit strain corresponds to the extension of the gauge length from 2.4" (61 mm) to 12" (305 mm).
(3) Lower the crosshead to 0% laminate fit strain with no hold; i.e., return to the original gauge length of 2.40" (61 mm).
(4) Strain the SRSL sample 151 to the specified laminate fit strain (400%) with no hold.
(5) Lower the crosshead to 300% laminate fit strain; i.e., to a gauge length of 9.6" (243.8 mm).
(6) Hold the SRSL sample 151 at 300% laminate fit strain for 2 minutes (Cycle 2, 300% unload laminate fit strain).
(7) Lower the crosshead to 200% laminate fit strain; i.e., to a gauge length of 7.2" (182.9 mm).
(8) Hold the SRSL sample 151 at 200% laminate fit strain for 2 minutes (Cycle 2, 200% unload laminate fit strain).
(9) Lower the crosshead to 150% laminate fit strain; i.e., to a gauge length of 6.0" (152.4 mm).
(10) Hold the SRSL sample 151 at 150% laminate fit strain for 2 minutes (Cycle 2, 150% unload laminate fit strain).
(11) Lower the crosshead to 100% laminate fit strain; i.e., to a gauge length of 4.8" (121.9 mm).
(12) Hold the SRSL sample 151 at 100% laminate fit strain for 2 minutes (Cycle 2, 100% unload laminate fit strain).
(13) Lower the crosshead to 0% laminate fit strain; i.e., return to the original gauge length of 2.40" (61 mm).

The reported second cycle unload forces of the SRSL, in Newtons (N), are the maximum unload forces measured during each two minute hold, at 300% laminate fit strain, 200% laminate fit strain, 150% laminate fit strain and 100% laminate fit strain.

A SRSL with a different unit length is within the scope of this method. The initial gauge length and final extended guage length (400% laminate fit strain) are selected so the SRSL is approximately 87% fully extended at 400% laminate fit strain. For different sample dimensions, the crosshead speed is adjusted to maintain the appropriate strain rate for each portion of the test. For example, a crosshead speed of 10"/min (25.4 cm/min) and a final extended gauge length of 6" (152.5 mm) would be used for a sample gauge length of 1.2" (30.5 mm).

EXAMPLES

Preparation of Elastic Material—Slow recovery elastic materials are prepared from a blend of about 48.5 percent by weight of the elastomeric polymer Vector 4211A (Dexco Polymers, Houston, Tex.) which comprises about 30 percent styrene by weight, about 48.5 percent by weight of the modifying resin Arkon P-140 (Arakawa Chemical Inc., Chicago, Ill.), and about 3 percent by weight of the mineral oil Britol 50T (Crompton Corporation, Petrolia, Pa.). The components are compounded in a twin-screw extruder, pelletized, and coated with powder to avoid blockage. The compounded pellets are melt cast extruded from a single-screw extruder into master film rolls during which a powder coating is added to avoid blockage, and the master film rolls are slit into narrow ribbons about 21 millimeters wide and puddle packed into boxes. Different basis weights of elastic material are made, ranging from about 120 to about 160 grams per square meter.

Figure 5:
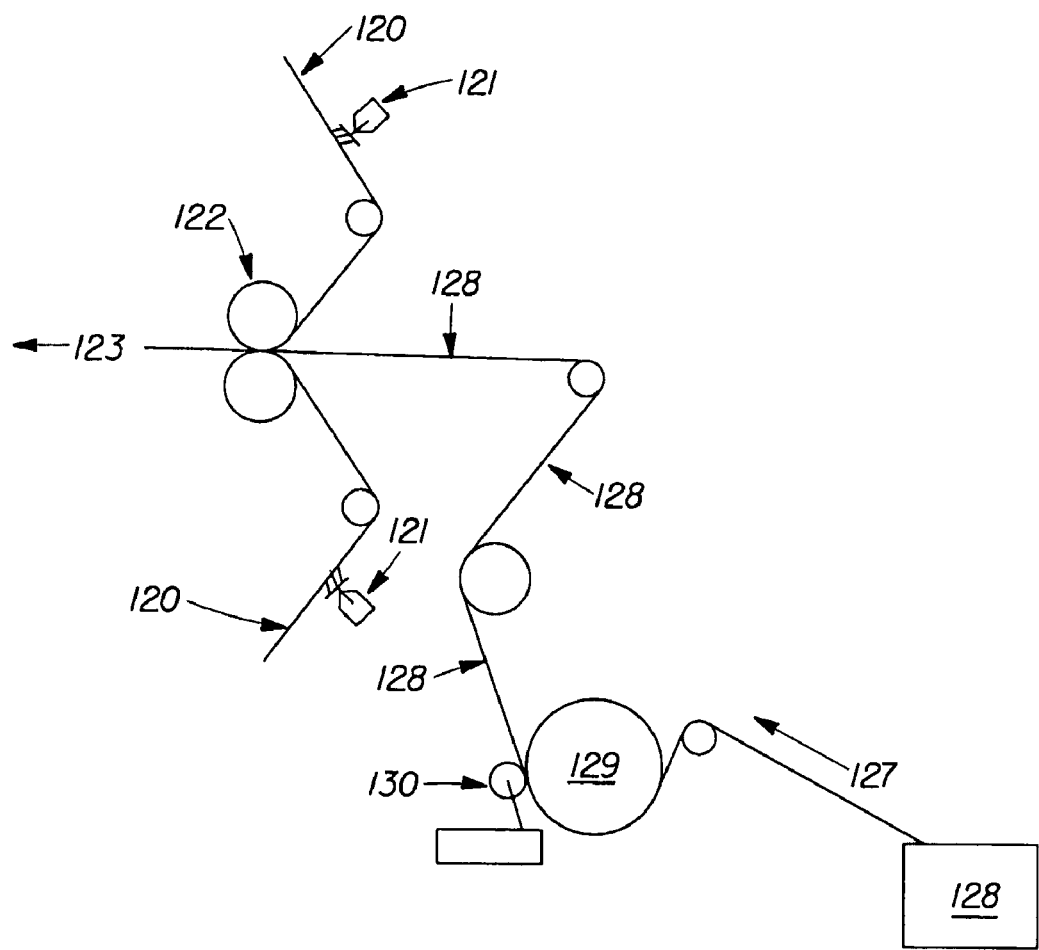
FIG. 5 is a schematic representation of a one-stage stretch lamination process for forming a slow recovery stretch laminate.

Laminate Preparation—SRSLs are prepared using a one-stage stretching unit such as shown in FIG. 5. The slow recovery elastic material 128 is pulled into the stretching unit by means of a heated roll 129 with a surface speed 127 of $V_{feed}$, is drawn down starting after the loading arm 130, is joined with two polypropylene based spunbond-meltblown-spunbond nonwovens 120 that have a basis weight of about 22 grams per square meter and an adhesive add on level of about 30 grams per square meter applied via applicator 121 in a pattern equivalent to about 15 to 25 lines per inch in the cross direction of manufacture of the laminate (Bostik H2401, Wauwatosa, Wis.), and is bonded to the nonwovens 120 in the elastic bonding unit 122 which consists of two water cooled stainless steel rolls set to a fixed narrow gap to yield a sufficiently strong bond, e.g., as measured by a peel strength test such as described in ASTM F904. The surface speed of the elastic bonding rolls are at the process pull velocity 123 of about 45 meters per minute, and the total path length between the heated roll 129 and the elastic bonding unit 122 is about 96.5 inches and equal to the span length over which the film stretching occurs.

SRSLs are made using the elastic materials and process conditions shown in Table 1. During the elastic draw down step the elastics stretched at room temperature exhibit non-uniform draw down (Examples 1 and 3). The width of the elastic varies in an approximate cyclical manner when observing the elastic at a fixed observation point between the heated roll and the elastic bonding roll. By contrast, the elastics stretched at a characteristic process temperature of about 40° C. exhibit uniform draw down (Examples 2 and 4).

TABLE 1

Slow Recovery Stretch Laminates

| Example number (laminate number) | Average basis weight of slow recovery elastic (grams per square meter) | Process strain (%) | Characteristic process temperature | Characteristic process strain rate (per minute) |
|---|---|---|---|---|
| 1 | 123 | 419 | Room temperature (approximately 22° C.) | 14.8 |
| 2 | 131 | 419 | 40° C. | 14.8 |
| 3 | 134 | 350 | Room temperature (approximately 22° C.) | 14.3 |
| 4 | 154 | 350 | 40° C. | 14.3 |

Tensile Test of Elastic Materials—Tensile tests of slow recovery elastic materials are performed at 22° C. and 40° C. For materials with a process strain of about 419%, cross-head speeds of about 15 and 62 inches per minute are used, and for materials with a process strain of about 350%, cross-head speeds of about 15 and 50 inches per minute are used. The cross-head speed of 15 inches per minute corresponds to the initial tensile strain rate being equal to the characteristic process strain rates from Table 1, and the 50 inches per minute and 62 inches per minute cross-head speeds correspond to the average tensile strain rate (up to the process strain) being equal to the characteristic process strain rates from Table 1. The average yield stress, post yield minimum stress, and yield stress drop are shown in Table 2, where the "none" entry indicates no observable yield drop in the engineering stress-strain curve, i.e., the yield stress drop is equal to zero. According to the present invention, the yield stress drops of Examples 5, 7, 9, and 11 indicate stability problems will occur with these elastic materials during draw down at room temperature and at the characteristic process strain rates of Table 1; whereas, the yield stress drops of Examples 6, 8, 10, and 12 indicate that heating these elastics to about 40° C. will minimize or eliminate stability problems during draw down at the characteristic process strain rates of Table 1. These results are consistent with the preparation of SRSLs with these elastic materials (Examples 1-4).

TABLE 2

Tensile yield results of slow recovery elastic materials*

| Example number | Average film basis weight (grams per square meter) | Tensile test cross-head speed (inches per minute) | Tensile test temperature (° C.) | Average yield stress (MPa) | Average post yield minimum stress (MPa) | Average yield stress drop (MPa) | Average yield stress drop (%) |
|---|---|---|---|---|---|---|---|
| 5 | 129 | 15 | 22 | 1.01 | 0.63 | 0.38 | 38 |
| 6 | 123 | 15 | 40 | 0.37 | 0.36 | 0.01 | 2.7 |
| 7 | 144 | 15 | 22 | 0.76 | 0.57 | 0.19 | 25 |
| 8 | 158 | 15 | 40 | 0.21 | none | 0.0 | 0.0 |
| 9 | 130 | 62 | 22 | 1.62 | 0.87 | 0.75 | 46 |

TABLE 2-continued

Tensile yield results of slow recovery elastic materials*

| Example number | Average film basis weight (grams per square meter) | Tensile test cross-head speed (inches per minute) | Tensile test temperature (° C.) | Average yield stress (MPa) | Average post yield minimum stress (MPa) | Average yield stress drop (MPa) | Average yield stress drop (%) |
|---|---|---|---|---|---|---|---|
| 10 | 126 | 62 | 40 | 0.63 | 0.50 | 0.13 | 21 |
| 11 | 140 | 50 | 22 | 1.01 | 0.67 | 0.34 | 34 |
| 12 | 159 | 50 | 40 | 0.31 | none | 0.0 | 0.0 |

*Averages based on 5 samples each for Examples 5, 7, 8, and 10-12, and on 7 samples each for Examples 6 and 9.

Two Cycle Fit Test of SRSLs—Two Cycle Fit Tests of the laminates from Table 1 (Examples 1-4) are performed at 22° C. and 37° C. Table 3 shows the average unload force and percent coefficient of variation for several unload laminate fit strains in the second cycle for a test temperature of 22° C. and Table 4 for a test temperature of 37° C. These results in combination with the tensile yield results in Table 2 show that SRSLs produced according to the present invention (Table 3, Examples 2 and 4, and Table 4, Examples 2 and 4) are much more reliable than those produced outside the present invention (Table 3, Examples 1 and 3, and Table 4, Examples 1 and 3).

TABLE 3

Second Cycle Unload Forces for SRSLs tested at 22° C. with Two Cycle Fit Test*

| Example Number | Laminate number from Table 1 | Characteristic process temperature | 300% unload laminate fit strain | | 200% unload laminate fit strain | | 150% unload laminate fit strain | | 100% unload laminate fit strain | |
|---|---|---|---|---|---|---|---|---|---|---|
| | | | Average Unload force (N) | % COV | Average Unload force (N) | % COV | Average Unload force (N) | % COV | Average Unload force (N) | % COV |
| 13 | 1 | Room temperature (approximately 22° C.) | 0.72 | 11% | 0.33 | 26% | 0.14 | 50% | 0.02 | 52% |
| 14 | 2 | 40° C. | 0.87 | 3% | 0.44 | 4% | 0.21 | 10% | 0.04 | 46% |
| 15 | 3 | Room temperature (approximately 22° C.) | 0.90 | 7% | 0.42 | 17% | 0.17 | 43% | 0.05 | 42% |
| 16 | 4 | 40° C. | 1.08 | 2% | 0.60 | 3% | 0.37 | 6% | 0.09 | 18% |

*Average unload forces and % COV (percent coefficient of variation) are based on 9 replicates per example except Example 15 with 11 replicates.

TABLE 4

Second Cycle Unload Forces for SRSLs tested at 37° C. with Two Cycle Fit Test*

| Example Number | Laminate number from Table 1 | Characteristic process temperature | 300% unload laminate fit strain | | 200% unload laminate fit strain | | 150% unload laminate fit strain | | 100% unload laminate fit strain | |
|---|---|---|---|---|---|---|---|---|---|---|
| | | | Average Unload force (N) | % COV* | Average Unload force (N) | % COV* | Average Unload force (N) | % COV* | Average Unload force (N) | % COV* |
| 17 | 1 | Room temperature (approximately 22° C.) | 0.65 | 10% | 0.34 | 18% | 0.18 | 42% | 0.04 | 51% |
| 18 | 2 | 40° C. | 0.79 | 3% | 0.46 | 4% | 0.29 | 6% | 0.09 | 19% |
| 19 | 3 | Room temperature (approximately 22° C.) | 0.79 | 9% | 0.43 | 16% | 0.24 | 31% | 0.06 | 56% |
| 20 | 4 | 40° C. | 0.98 | 3% | 0.59 | 4% | 0.39 | 5% | 0.14 | 15% |

*Average unload forces and % COV (percent coefficient of variation) are based on 9 replicates per example except Example 15 with 11 replicates.

Examples 21-23 are meant to illustrate specific SRSL sampling, testing, and calculation of the percent coefficient of variation for each type of article element as referenced in connection with definition of "reliable" above.

Example 21

This example illustrates the computation of the percent coefficient of variation for the case where an absorbent article comprises an article element comprising a SRSL, and where the consumer-sized package contains five or more absorbent articles. For example, if a package of absorbent articles contains 24 disposable diapers and each diaper has a leg cuff made from a SRSL, then five diapers would be randomly chosen from the 24, the leg cuff of interest would be carefully removed from the identical position on each of the five randomly chosen absorbent articles; the unload force at 37° C. and the initial strain after 15 seconds at 22° C. would be measured on the leg cuff SRSL according to the Two-Cycle Hysteresis Test and the Post Elongation Recovery Test, respectively. The results from each of the five diapers would be illustrated as shown in Table 5, along with the corresponding values of the arithmetic average, standard deviation, and percent coefficient of variation for each measurement. In Table 5, the arithmetic average is computed according to Equation [10]

$$\bar{x} = \frac{1}{n}\sum_{i=1}^{n} x_i = \frac{x_1 + x_2 + \ldots + x_n}{n} \quad [10]$$

where $\bar{x}$ is the arithmetic average, n the number of samples tested (5 in this example), and $x_i$ the measured value of either the unload force at 37° C. or the initial strain after 15 seconds at 22° C. for the $i^{th}$ test sample. In Table 5, the standard deviation is computed according to Equation [11]

$$\sigma = \sqrt{\frac{1}{n}\sum_{i=1}^{n}(x_i - \bar{x})^2} \quad [11]$$

where $\sigma$ is the standard deviation. In Table 5, the percent coefficient of variation is computed according to Equation [12]

$$\% \text{ COV} = (100)\frac{\sigma}{\bar{x}} \quad [12]$$

where % COV is the percent coefficient of variation.

TABLE 5

|  | Article Element = Leg Cuff Unload force at 37° C. | Article Element = Leg Cuff Percent of initial strain after 15 seconds at 22° C. |
|---|---|---|
| Test Absorbent Article 1 | 0.23 N/(g/m) | 50% |
| Test Absorbent Article 2 | 0.25 N/(g/m) | 52% |
| Test Absorbent Article 3 | 0.26 N/(g/m) | 48% |
| Test Absorbent Article 4 | 0.23 N/(g/m) | 47% |
| Test Absorbent Article 5 | 0.21 N/(g/m) | 55% |
| Arithmetic average | 0.24 N/(g/m) | 50% |
| Standard deviation | 0.019 N/(g/m) | 3.2% |
| Percent coefficient of variation | 7.9% | 6.4% |

Example 22

This example illustrates the computation of the percent coefficient of variation for the case where an absorbent article comprises two article elements comprising a SRSL, and where the consumer-sized package contains less than five absorbent articles. For example, if a package of absorbent articles contains two disposable diapers and each diaper has a leg cuff comprising a SRSL and an elasticized topsheet comprising a SRSL, then five diapers would be randomly chosen from combining at least three such packages (e.g., same lot, same size, etc.). The leg cuff of interest would be carefully removed from the identical position on each of the five randomly chosen absorbent articles and the elasticized topsheet of interest would be carefully removed from the identical position on each of the five randomly chosen absorbent articles. The unload force at 37° C. and the initial strain after 15 seconds at 22° C. would be measured on each of the leg cuff and elasticized topsheet SRSLs according to the Two-Cycle Hysteresis Test and the Post Elongation Recovery Test, respectively. The results from each of the five diapers would be illustrated as shown in Table 6; the arithmetic average, standard deviation, and percent coefficient of variation are computed using Equations [10]-[12], respectively.

TABLE 6

|  | Article Element = Leg Cuff Unload force at 37° C. | Article Element = Leg Cuff Percent of initial strain after 15 seconds at 22° C. | Article Element = Elasticized Topsheet Unload force at 37° C. | Article Element = Elasticized Topsheet Percent of initial strain after 15 seconds at 22° C. |
|---|---|---|---|---|
| Test Absorbent Article 1 | 0.23 N/(g/m) | 50% | 0.34 N/(g/m) | 100% |
| Test Absorbent Article 2 | 0.25 N/(g/m) | 52% | 0.33 N/(g/m) | 110% |
| Test Absorbent Article 3 | 0.26 N/(g/m) | 48% | 0.36 N/(g/m) | 105% |
| Test Absorbent Article 4 | 0.23 N/(g/m) | 47% | 0.36 N/(g/m) | 96% |
| Test Absorbent Article 5 | 0.21 N/(g/m) | 55% | 0.35 N/(g/m) | 104% |
| Arithmetic average | 0.24 N/(g/m) | 50% | 0.35 N/(g/m) | 103% |
| Standard deviation | 0.019 N/(g/m) | 3.2% | 0.013 N/(g/m) | 5.3% |
| Percent coefficient of variation | 7.9% | 6.4% | 3.7% | 5.1% |

Example 23

This example illustrates the computation of the percent coefficient of variation for the case where an absorbent article comprises one article element comprising a SRSL and a second article element comprising two SRSLs, and where the consumer-sized package contains less than five absorbent articles. For example, if a package of absorbent articles contains 2 disposable diapers and each diaper has a leg cuff made from a SRSL and an elasticized topsheet made from two SRSLs, then five diapers would be randomly chosen from combining at least three such packages (e.g., same lot, same size, etc.). The leg cuff of interest would be carefully removed from the identical position on each of the five randomly chosen absorbent articles, the first SRSL from the elasticized topsheet of interest would be carefully removed from the identical position on each of the five randomly chosen absorbent articles, and the second SRSL from the elasticized topsheet of interest would be carefully removed from the identical position on each of the five randomly chosen absorbent articles. The unload force at 37° C. and the initial strain after 15 seconds at 22° C. would be measured on each of the leg cuff and elasticized topsheet SRSLs according to the Two-Cycle Hysteresis Test and the Post Elongation Recovery Test, respectively. The results from each of the five diapers would be illustrated as shown in Table 7; the arithmetic average, standard deviation, and percent coefficient of variation are computed using Equations [10]-[12], respectively.

TABLE 7

|  | Article Element = Leg Cuff Unload force at 37° C. | Article Element = Leg Cuff Percent of initial strain after 15 seconds at 22° C. | Article Element = Elasticized Topsheet (SRSL #1) Unload force at 37° C. | Article Element = Elasticized Topsheet (SRSL #1) Percent of initial strain after 15 seconds at 22° C. | Article Element = Elasticized Topsheet (SRSL #2) Unload force at 37° C. | Article Element = Elasticized Topsheet (SRSL #2) Percent of initial strain after 15 seconds at 22° C. |
|---|---|---|---|---|---|---|
| Test Absorbent Article 1 | 0.23 N/(g/m) | 50% | 0.34 N/(g/m) | 100% | 0.32 N/(g/m) | 105% |
| Test Absorbent Article 2 | 0.25 N/(g/m) | 52% | 0.33 N/(g/m) | 110% | 0.31 N/(g/m) | 107% |
| Test Absorbent Article 3 | 0.26 N/(g/m) | 48% | 0.36 N/(g/m) | 105% | 0.29 N/(g/m) | 110% |
| Test Absorbent Article 4 | 0.23 N/(g/m) | 47% | 0.36 N/(g/m) | 96% | 0.29 N/(g/m) | 115% |
| Test Absorbent Article 5 | 0.21 N/(g/m) | 55% | 0.35 N/(g/m) | 104% | 0.33 N/(g/m) | 104% |
| Arithmetic average | 0.24 N/(g/m) | 50% | 0.35 N/(g/m) | 103% | 0.31 N/(g/m) | 108% |
| Standard deviation | 0.019 N/(g/m) | 3.2% | 0.013 N/(g/m) | 5.3% | 0.018 N/(g/m) | 4.4% |
| Percent coefficient of variation | 7.9% | 6.4% | 3.7% | 5.1% | 5.8% | 4.1% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

What is claimed is:

1. A package of absorbent articles, comprising:
a plurality of absorbent articles contained within the package, wherein each absorbent article in the package comprises:
 a) a topsheet;
 b) a backsheet joined with the topsheet;
 c) an absorbent core interposed between the topsheet and backsheet; and
 d) an article element;
wherein at least one article element for each absorbent article in the package comprises a slow recovery stretch laminate exhibiting an unload force at 37° C. of about 0.16 N/(g/m) or greater and a percent of initial strain after 15 seconds of recovery at 22° C. of about 10% or greater;
wherein the slow recovery stretch laminate exhibits a percent coefficient of variation of greater than zero and less than about 15% for the unload force at 37° C. and a percent coefficient of variation of greater than zero and less than about 15% for the initial strain after 15 seconds of recovery at 22° C.; and
wherein the slow recovery stretch laminate is produced in a continuous process.

2. The package of absorbent articles of claim 1 wherein the article element is selected from the group consisting of an anal cuff, an elasticized topsheet, a fastening system, a leg cuff, a waist elastic feature, a side panel, an ear, an outer cover, and combinations thereof.

3. The package of absorbent articles of claim 1 wherein the slow recovery stretch laminate for each of the absorbent articles within the package exhibits a percent of initial strain after 15 seconds of recovery at 22° C. of about 30% or greater.

4. The package of absorbent articles of claim 1 wherein the slow recovery stretch laminate for each of the absorbent articles within the package exhibits a percent of initial strain after 15 seconds of recovery at 32° C., wherein the difference of the percent of initial strain after 15 seconds of recovery at 22° C. and the percent of initial strain after 15 seconds of recovery at 32° C. is greater than about 5%.

5. The package of absorbent articles of claim 1 wherein the slow recovery stretch laminate for each of the absorbent articles within the package comprises
   a) at least a first substrate having a first surface and a second surface
   b) at least one elastic member joined or attached to the first surface of the substrate.

6. The package of absorbent articles of claim 5 wherein the slow recovery stretch laminate for each of the absorbent articles within the package further comprises a second substrate having a first surface and a second surface, wherein the elastic member is joined to the first surface of the second substrate such that the elastic member is disposed between the first substrate and the second substrate.

7. The package of absorbent articles of claim 5 wherein the elastic member of the slow recovery stretch laminate for each of the absorbent articles within the package is joined or attached to the first surface of the substrate via a method selected from the group consisting of adhesive bonding, thermal bonding, pressure bonding, ultrasonic bonding, and combinations thereof.

8. The package of absorbent articles of claim 5 wherein the elastic member of the slow recovery stretch laminate for each of the absorbent articles within the package comprises
   a) about 20% to about 100% of at least one elastomeric polymer,
   b) optionally, about 0.01% to about 60% of at least one modifying resin; and
   c) optionally, about 0.01% to about 60% of at least one additive.

9. The package of absorbent articles of claim 8 wherein the elastomeric polymer is selected from a group comprising styrenic block copolymers, natural and synthetic rubbers, polyisoprene, neoprene, polyurethanes, silicone rubbers, hydrocarbon elastomers, ionomers, and combinations thereof.

10. The package of absorbent articles of claim 9 wherein the elastomeric polymer is a block copolymer comprising at least one substantially soft block and at least one substantially hard block.

11. The package of absorbent articles of claim 8 wherein the modifying resin for each of the absorbent articles within the package is selected from a group comprising unhydrogenated C5 hydrocarbon resins or C9 hydrocarbon resins, partially and fully hydrogenated C5 hydrocarbon resins or C9 hydrocarbon resins; cycloaliphatic resins; terpene resins; polystyrene and styrene oligomers; poly(t-butylstyrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof.

12. The package of absorbent articles of claim 5 wherein the elastic member of the slow recovery stretch laminate for each of the absorbent articles within the package is in a form selected from a group comprising a film, a strand, a band, a cross-hatch array, a foam, and combinations thereof.

13. The package of absorbent articles of claim 5 wherein the first substrate for each of the absorbent articles within the package is selected from a group comprising nonwoven webs, woven webs, knitted fabrics, films, film laminates, apertured films, nonwoven laminates, sponges, foams, scrims, and combinations thereof.

14. The package of absorbent articles of claim 1 wherein each of the absorbent articles within the package is selected from a group comprising diapers, training pants, pull-on garments, refastenable pants, adult incontinence products, or feminine care products.

15. The package of absorbent articles of claim 5 wherein the elastic member of the slow recovery stretch laminate for each of the absorbent articles within the package is pretreated prior to and/or during draw down of the elastic member.

16. The package of absorbent articles of claim 15 wherein the pretreatment of the elastic member of the slow recovery stretch laminate for each of the absorbent articles within the package is selected from a group comprising heating, pre-stretching, incrementally stretching, and combinations thereof.

17. The package of absorbent articles of claim 16 wherein the elastic member of the slow recovery stretch laminate for each of the absorbent articles within the package is heated to a temperature from about 30 to about 100° C. prior to and/or during draw down of the elastic member.

18. The package of absorbent articles of claim 5 wherein the elastic member of the slow recovery stretch laminate for each of the absorbent articles within the package exhibits one or more of the following:
   (i) a yield stress drop of about 0.3 MPa or less at the characteristic strain rate and characteristic temperature of the stretching process;
   (ii) a percent yield stress drop of about 30 percent or less at the characteristic strain rate and characteristic temperature of the stretching process;
   (iii) a yield stress drop of about 0.15 MPa or less at the initial tensile strain rate equal to the characteristic strain rate of the stretching process and at the characteristic temperature of the stretching process; and
   (iv) a percent yield stress drop of about 20 percent or less at the initial tensile strain rate equal to the characteristic strain rate of the stretching process and at the characteristic temperature of the stretching process.

19. The package of absorbent articles of claim 1 wherein the slow recovery stretch laminate exhibits a percent coefficient of variation of greater than zero and less than about 10% for the unload force at 37° C. and a percent coefficient of variation of greater than zero and less than about 10% for the initial strain after 15 seconds of recovery at 22° C.

20. An absorbent article comprising:
   a) a topsheet;
   b) a backsheet joined with the topsheet;
   c) an absorbent core interposed between the topsheet and backsheet; and
   d) an article element selected from the group consisting of an anal cuff, an elasticized topsheet, a fastening system, a leg cuff, a waist elastic feature, a side panel, an ear, an outer cover, and combinations thereof;
   wherein said article element comprises a slow recovery stretch laminate exhibiting an unload force at 37° C. of about 0.16 N/(g/m) or greater and a percent of initial strain after 15 seconds of recovery at 22° C. of about 10% or greater;
   wherein the slow recovery stretch laminate comprises an elastic member that is pretreated prior to and/or during draw down of the elastic member; and
   wherein the slow recovery stretch laminate is produced in a continuous process.

* * * * *